United States Patent
Shokat et al.

(10) Patent No.: US 6,610,483 B1
(45) Date of Patent: Aug. 26, 2003

(54) METHODS FOR IDENTIFYING CELLULAR RESPONSES ATTRIBUTABLE TO SIGNALING MOLECULE INHIBITION AND INHIBITORS THEREOF

(75) Inventors: Kevan M. Shokat, San Francisco, CA (US); Anthony Bishop, San Diego, CA (US)

(73) Assignee: Princeton University, Princeton, NJ (US)

( * ) Notice: Subject to any disclaimer, the term of this patent is extended or adjusted under 35 U.S.C. 154(b) by 0 days.

(21) Appl. No.: 09/621,293

(22) Filed: Jul. 20, 2000

Related U.S. Application Data

(60) Provisional application No. 60/145,422, filed on Jul. 23, 1999.

(51) Int. Cl.$^7$ .......................... C12Q 1/68; G01N 33/53; C12P 21/00; C07H 21/04; C12N 5/10

(52) U.S. Cl. .............................. 435/6; 435/7.1; 435/7.2; 435/7.4; 435/69.1; 435/183; 435/194; 435/325; 435/343; 536/23.1

(58) Field of Search ......................... 435/6, 69.1, 194, 435/325, 343, 7.1, 7.2, 7.4, 183; 536/23.1

(56) References Cited

U.S. PATENT DOCUMENTS

| | | | | |
|---|---|---|---|---|
| 5,352,660 | A | * 10/1994 | Pawson ........................ | 514/12 |
| 5,443,962 | A | * 8/1995 | Draetta et al. .................. | 435/6 |
| 5,593,997 | A | * 1/1997 | Dow et al. ..................... | 514/258 |
| 5,731,343 | A | * 3/1998 | Feng et al. .................... | 514/450 |
| 5,800,992 | A | 9/1998 | Fodor et al. ..................... | 435/6 |
| 5,965,352 | A | * 10/1999 | Stoughton et al. ............. | 435/4 |
| 6,019,966 | A | 2/2000 | Coleman et al. ............ | 424/94.5 |
| 6,100,254 | A | * 8/2000 | Budde et al. ................ | 514/221 |
| 6,162,613 | A | 12/2000 | Shin-Sau et al. ............. | 435/6 |
| 6,251,911 | B1 | * 1/2001 | Bold et al. ................... | 514/258 |
| 6,383,790 | B1 | 5/2002 | Shokat ........................ | 435/194 |
| 6,390,821 | B1 | 5/2002 | Shokat ........................ | 434/194 |

FOREIGN PATENT DOCUMENTS

| | | |
|---|---|---|
| WO | WO 98/35048 | 8/1998 |
| WO | WO 99/42592 | 8/1999 |

OTHER PUBLICATIONS

Belshaw et al., Rational design of orthogonal receptor–ligand combinations, Angw. Chem. Int. Ed. Engl. 34:2129–2132 (1995).

Bishop et al., Design of allele–specific inhititors to probe protein kinase signalling, Curr. Biol. 8:257–266 (1998).

Bishop et al., Generation of monospecific nanomolar tyrosine kinase inhibitors via a chemical genetic approach, J. Am. Chem. Soc. 121:627–631 (1999).

Bishop et al., Acquisition of inhibitor–sensitive protein kinases through protein design, Pharmacol. Therapeut. 82:337–346 (1999).

Bishop et al., A chemical switch for inhibitor–sensitive alleles of any protein kinase, Nature 407:395–401 (2000).

Bolen et al., The Src family of tyrosine protein kinases in hemopoietic singnal transduction, FASEB J. 6:3403–3409 (1992).

Brown et al., Regulation, substrantes and functions of Src, Biochemica et Biophysica Acta 1287:121–149 (1996).

Brugge et al., Identificaiton of a transformation–specific antigen induced by an avian sarcoma virus, Nature 269:346–348 (1977).

Cicchetti et al., Identification of a protein that binds to the SH3 region of Abl and is similar to Bcr and GAP–rho, Science 257:803–806 (1992).

Cohen et al., Modular binding domains in signal transduction proteins, Cell 80:237–248 (1995).

Eck et al., SH2 crystal structure, Nature 362:87–91 (1993).

Eiseman, Engagement of the high–affinity IgE receptor activates src protein–related tyrosine kinases, Nature 355:78–80 (1992).

Erpel et al., Src family protein tyrosine kinases and cellular signal transduction pathways, Curr. Opin. Cell Biol. 7:176–182 (1995).

Faltynek et al., Damnacanthal is a highly potent, selective inhibitor of p56$^{lck}$ tyrosine kinase activity, Biochem. 434:12404–12410 (1995).

Hanke et al., Discovery of a novel, potent Src–family selective tyrosine kinase inhibitor, J. Biol. Chem. 271:695–701 (1996).

Hanks et al., Protein kinase catalytic domain sequence database: Identification of conserved features of primary structure and classification of family members, Methods in Enzymology, 200:38–81 (1991).

Hunter, A thousand and one protein kinases, Cell 50:823–829 (1987).

Hunter, Protein kinases and phosphatases: the yin and yang of protein phosphorylation and signaling, Cell 80:225–236 (1995).

Hwang et al., A Mutation that Alters the Nucleotide Specificity of Elongation Factor Tu, a GTP Regulatory Protein, J. Biol. Chem. 262:13081–13085 (1987).

(List continued on next page.)

*Primary Examiner*—Stephanie Zitomer
(74) *Attorney, Agent, or Firm*—Morgan, Lewis & Bockius LLP

(57) ABSTRACT

The present invention provides a method for the identification of a pattern of changes in cellular responses induced by the selective inhibition of a signaling molecule, by determining the specific effects of a selective inhibitor on a mutant form of a signaling molecule on cellular responses. The pattern of alterations in cellular responses resulting from the inhibition by a selective mutant inhibitor of the mutant signaling molecule are characteristic of the cellular response alterations that a specific inhibitor of the wild-type signaling molecule will produce. After determining the pattern of cellular responses of the mutant cells with the mutant molecule, compounds may be identified capable of inhibiting the wild-type molecule by producing a pattern of cellular responses in wild-type cells matching or having similarity to that of the inhibition of the mutant molecule.

28 Claims, 13 Drawing Sheets

OTHER PUBLICATIONS

Jove et al., Cell transformation by the viral src oncogene, Ann. Rev. Cell. Biol. 3:31–56 (1987).

Kamps et al., Most of the substrates of oncogenic viral tyrosine protein kinases can be phosphorylated by cellular tyrosine protein kinases in normal cells, Oncogene Res. 3:105–115 (1988).

Kipreos et al., Cell cycle–regulated binding of c–abl tyrosine kinase to DNA, Science 256:382–385 (1992).

Koyama et al., Structure of the PI3K SH3 domain and analysis of the SH3 Family, Cell 72:945–952 (1993).

Liu et al., A molecular gate which controls unnatural ATP analogue recognition by the tyrosine kinase v–Src, Bioorganic Med. Chem. 6:1219–1226 (1998).

Liu et al., Structural basis for selective inhibition of Src family kinases of PP1, Chem. Biol. 6:671–678 (1999).

Mayer et al., Point mutations in the ab1 SH2 domain coordinately impair phosphotyrosine binding in vitro and transforming activity in vivo, Mol. Cell. Biol. 12:609–618 (1992).

Mayer et al., Mutagenic analysis of the roles of SH2 and SH3 domains in regulation of the ab1 tyrosine kinase, Mol. Cell. Biol. 14:2883–2894 (1994).

Mustelin, T Cell antigen receptor signaling: three families of tyrosine kinases and a phosphatase, Immunity 1:351–356 (1994).

Pawson, Protein modules and signalling networks, Nature 373:573–580 (1995).

Renshaw et al., Oncogenic v–Abl tyrosine kinase can inhibit or stimulate growth, depending on the cell context, EMBO J. 11:3941–3951 (1992).

Sawyers et al., The nuclear tyrosine kinase c–Abl negatively regulates cell growth, Cell 77:121–131 (1994).

Songyang et al., Catalytic specificity of protein–tyrosine kinases is critical for selective signalling, Nature 373:536–539 (1995).

Taylor et al., The cell cycle and c–Src, Curr. Opin. Genet. Dev. 3:26–34 (1993).

Ullrich et al., Signal transduction by receptors with tyrosine kinase activity, Cell 61:203–212 (1990).

Velazquez et al., A protein tyrosine kinase in the interferon alpha/beta signaling pathway, Cell 70:313–320 (1992).

Waksman et al., Crystal structure of the phosphotyrosine recognition domain SH2 of v–src complexed with tyrosine-phosphorylated peptides, Nature 358:646–653 (1992).

Waksman et al., Binding of a high affinity phosphotyrosyl peptide to the Src SH2 domain: crystal structures of the complexed and peptide–free forms, Cell 72:779–790 (1993).

Weijland et al., Toward a Model for the Interaction Between Elongation Factor Tu and the Ribosome, Science 259:1311–1314 (1993).

Yu et al., Solution Structure of the SH3 domain of Src and identification of its ligand–binding site, Science 258:1665–1668 (1992).

International Search Report from PCT/US00/19912 (dated Jan. 25, 2001).

* cited by examiner

Transcriptional Non-Specific Drug Effects of 500nM

CDC28      CDC28
           Inhibitor 30 minutes treatment
7 genes altered (of >6200)

2 hours treatment
3 genes altered (of >6200)

Transcriptional Effects of F88G Mutation in CDC28

Lysed at $OD_{600} = 0.7$
22 genes altered (of >6200)

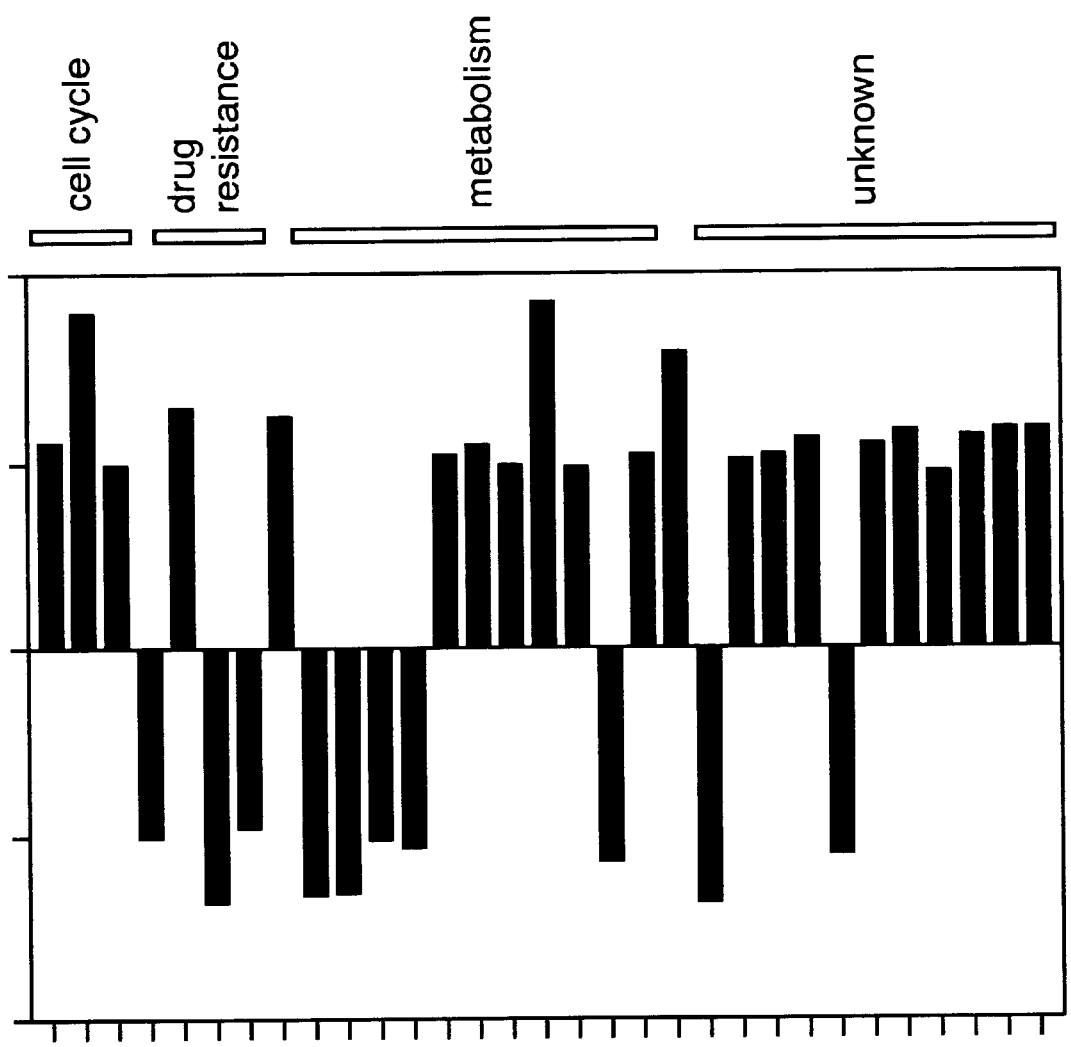

Transcriptional Effects of Specific Inhibition of F88G CDC28 (30 min)

Transcriptional Effects of Specific Inhibition of F88G CDC28 (2 hr)

FIG. 5A

| Gene Name | Function | Fold Change |
|---|---|---|
| I. Gene transcription increased after 30 minute exposure to 500 nM 4-amino-1-(tert-butyl)-3-(1'-naphthylmethyl)pyrazolo[3,4-d]pyrimidine | | |
| YLR452C/ssT2_at | Protein involved in desensitization to alpha-factor pheromone | 2.8 |
| YDL216c/_at | Protein of unknown function | ~1.6 |
| YDR461w/MFA1_at | Mating pheromone a-factor; exported from cell by Ste6p | 4.9 |
| YFR002W/NIC96_at | Nuclear pore protein (nucleoporin); acts in a complex with Nsp1p, Nup57p, and Nup49p | 3.1 |
| YJL221C/FSP2_f_at | Protein with similarity to alpha-D-glucosidase (maltase) (D43761) (FSP2 and YIL172C code for identical proteins) | ~2.3 |
| YRL042c/_at | Protein of unknown function | 2.2 |
| YMR251W/_at | Protein of unknown function | ~1.8 |
| YNL270C/ALP1_at | Protein with strong similarity to permeases Can1p and Lyp1p for basic amino acids | ~2.0 |
| YNR044W/AGA1_at | a-Agglutinin anchor subunit | 3.2 |
| YOR391C/_1_at | Protein of unknown function | 1.7 |
| YPL041C/_at | Protein of unknown function | 2.6 |
| II. Gene transcription decreased after 30 minute exposure to 500 nM 4-amino-1-(tert-butyl)-3-(1'-naphthylmethyl)pyrazolo[3,4-d]pyrimidine | | |
| YAR018C/KIN3_at | MCM cluster; Serine/threonine protein kinase; null mutant has no phenotype | ~3.2 |
| YAR071W/PH011_f_at | Acid phosphatase, secreted | ~2 |
| YBL002W/HT82_at | Histone H2B; | ~4.1 |
| YBL003c/HTA2_at | Histone H2A | ~3.6 |
| YBL096c/_at | Protein of unknown function, probably not an expressed ORF | ~2.2 |
| YBR009c/HHF1_f_at | Histone H4 | ~2.2 |
| YBR010w/HHT1_at | Histone H3 | ~2 |
| YBR038w/CHS2_at | Clb2 cluster; Chitin synthase II, responsible for primary septum disk | ~3.5 |
| YBR092c/PH03_at | Acid phosphatase, constitutive, thiamine-binding protein of the periplasmic space | ~3.1 |
| YBR158w/_at | Protein required for optimal growth and germination rate | ~2.2 |
| YBR202w/CDC47_at | MCM cluster; Member of MCM/P1 family of proteins involved in DNA synthesis initiation | ~2.2 |
| YCL062w/_at | Clb2 cluster; Protein involved in sensitivity to certain drugs; has similarity to plant aminocyclopropane-1-carboxylate synthase | ~1.9 |
| YCL064c/CHA1_at | L-serine/L-threonine-deaminase | ~2.0 |
| YCR005c/CIT2_at | Citrate synthase, peroxisomal (nonmitochondrial), converts acetyl-CoA and oxaloacetate into citrate CoA | ~2.3 |
| YDL179w/_at | Cyclin, associates with Pho85p | ~4.0 |
| YDR033w/_at | Protein with similarity to Yro2p | ~2.6 |
| YDR089w/_at | Protein of unknown function; has leucine zipper | ~2.3 |
| YDR097C/_at | Component with Msh2p of DNA mismatch binding factor; involved in repair of single base mismatches | ~2.1 |
| YDR113c/PDSI_at | Protein that may regulate sister chromatid separation in mitosis | ~1.6 |
| YDR146c/SWI5_at | Clb2 cluster; Transcription factor that controls cell cycle-specific transcription of HO | ~3.4 |
| YDR331W/_at | Protein involved in the attachment of glycosylphosphatidylinositol(GPI) anchors to proteins | ~1.7 |
| YDR370C/_at | Protein of unknown function | ~2 |
| YER067w/_at | Protein of unknown function | ~3.6 |
| YER070w/RNR1_at | Ribonucleotide reductase (ribonucleoside-diphosphate reductase) large subunit; converts deoxyribonucleoside diphosphate to ribonucleoside | ~2 |

FIG. 5B

| Gene Name | Function | Fold Change |
|---|---|---|
| YER113c/_at | Protein with similarity to Emp70p | ~-2.0 |
| YER124c/_at | Protein of unknown function | ~-3.0 |
| YGL021W/ALK1_at | Clb2 cluster; DNA damage-responsive protein | ~-2.9 |
| YGL028C/_at | Putative cell wall protein with similarity to Scw10p | ~-2.8 |
| YGL086W/MAD1_at | Coiled-coil protein involved in spindle-assembly checkpoint; required for cell cycle delay in response to impaired kinetochore function | ~-2 |
| YGL116W/CDC20_at | Clb2 cluster; Protein required for microtubule function at mitosis; member of WD (WD-40) repeat family | ~-2.5 |
| YGL237C/HAP2_at | Component (with Hap3p, Hap4p, and hap5p) of heterotrimeric CCAAT-binding factor, has a highly conserved core region of 60 amino acids | ~-2.7 |
| YGR044C/RME1_at | Zinc-finger transcription factor that represses meiosis in non-a/alpha cells | ~-2 |
| YGR108W/CLB1_at | Clb2 cluster; G2/M-phase-specific cyclin | ~-3.8 |
| YGR177C/ATF2_at | Sterol O-acetyltranferase; acetylates certain toxic steroids such as pregnenolone to render them excretable | ~-1.9 |
| YGR230W/_at | MCM cluster; Protein with similarity to Spo12p, able to partially suppress requirement for Spo12p in meiosis | ~-3.8 |
| YHR023W/MYO1_at | Clb2 cluster; Myosin heaavy chain (myosin II), coiled-coil protein involved in septation and cell wall organization | ~-2.9 |
| YHR152w/SPO12_at | Sporulation protein required for chromosome division in meiosis I | ~-2.1 |
| YIL106W/MOB1_at | Clb2 cluster; Protein required for completion of mitosis and maintenance of ploidy | ~-3.0 |
| YIL131C/FKH1_at | Homolog of Drosophila forkhead protein | ~-2.1 |
| YIL158W/_at | Clb2 cluster; Protein with similarity to Ykr100p | ~-5.4 |
| YJL051W/_at | Clb2 cluster; Protein of unknown function | ~-5.5 |
| YJL062W/_at | Protein required for addition of a side chain to the glycosylphospatidylinositol (GPI) core structure | ~-2.3 |
| YJL074C/SMC3_at | Cohesion, Coiled-coil protein of the SMC family involved in chromosome condensation and segregation | ~-2.1 |
| YJL078C/PRY3_at | Protein with similarity to plant pathenogenesis-related proteins | ~-2.1 |
| YJR092W/BUD4_at | Clb2 cluster; Protein required for axial budding but not for bipolar budding | ~-2.3 |
| YKL049C/CSE4_at | Protein with similarity to histone H3, required for chromosome segregation | ~-2.5 |
| YKL185W/ASH1_at | GATA-type transcription factor, negative regulator of HO expression localized preferentially in daughter cells | ~-2 |
| YLR049c/_at | Protein of unknown function | ~-2.9 |
| YLR057w/_at | Clb2 cluster; Protein of unknown function | ~-2.3 |
| YLR131c/ACE2_at | Clb2 cluster; Metallothionein expression activator with similarity to Swi5p | ~-2.5 |
| YLR190W/_at | Clb2 cluster; Protein of unknown function | ~-2.5 |
| YLR254C/_at | Protein of unknown function | ~-2.1 |
| YLR373C/_at | Protein with weak similarity to Von Wiflebrand factor | ~-2.2 |
| YML033W/_at | Clb2 cluster; Protein of unknown function | ~-2.7 |
| YML034/_at | Clb2 cluster; Protein of unknown function | ~-2.7 |
| YML052W/_at | G2/M peak; Protein of unknown function; overproduction suppresses the rvs167 mutation | ~-2.4 |
| YML119W/_at | Clb2 cluster; Protein of unknown function | ~-3.2 |
| YMR001C/CDC5_at | Clb2 cluster; Serine/threonine kinase required for exit from mitosis | ~-3.4 |
| YMR011W/HXT2_at | High-affinity hexose transporter; member of sugar permease family | ~4.7 |
| YMR032W/_at | Clb2 cluster; Protein involved in cytokinesis | ~-3.5 |
| YMR215W/_at | Protein with similarity to Gas1p | ~-2.4 |
| YNL046W/_at | Protein of unknown function | ~-3 |
| YNL058C/_at | Clb cluster; Protein of unknown function | ~-3.2 |
| YNL171C/_at | Protein of unknown function, questionable ORF | ~-1.8 |
| YNL327W/_at | Cell-cycle regulation protein; may be involved in the correct timing of cell separation after cytokinesis | ~-3 |

FIG. 5C

| Gene Name | Function | Fold Change |
|---|---|---|
| YNR067C/_at | Protein of unknown function | -4.8 |
| YOL070C/_at | Protein of unknown function | -3.1 |
| YOR025W/HST3_at | Clb2 cluster, Protein with similarity to Sir2p | -5.0 |
| YOR264W/_at | Protein of unknown function | -2.5 |
| YOR315W/_at | Protein of unknown function | -4.7 |
| YPL141C/_at | LPI5; Serine/threonine protein kinase with similarity to Kin4p | -3 |
| YPL242C/_at | Clb2 cluster; IQG1 Protein involved in cytokinesis; has similarity to mammalain IQGAP proteins | -2.3 |
| YPR119W/_at | Clb2 cluster; Clb2 G2/M-phase-specific cyclin | -5.9 |
| YPR202W/_ex1_f_at | Protein with similarity to other subtelometrically-encoded proteins | -2.2 |

III. Gene transcription increased after 120 minute exposure to 500 nM 4-amino-1-(tert-butyl)-3-(1'-naphthylmethyl)pyrazolo[3,4-d]pyrimidine

| Gene Name | Function | Fold Change |
|---|---|---|
| YAR068W/_at | Protein with similarity to ICWP protein | -4.5 |
| YBL016w/FUS3_at | Serine/threonine protein kinase required for cell cycle and for cell fusion during mating; member of the MAP kinase family | 2.4 |
| YBL106c/_at | SRO77; Sec9-interacting protein, involved in secretory pathway and Na+ homeostasis | -2.5 |
| YBR108W/_at | Protein with weak similarity to wheat glutenin, secalin, and Drosophila mastermind protein | -2.4 |
| YBR115c/LYS2_at | Alpha-aminoadipate-semialdehyde dehydrogenase large chain, sixth step in lysine biosynthesis pathway | 2.4 |
| YBR222c/FAT2_at | Peroxisomal AMP-binding protein | 2.4 |
| YBR299w/MAL32_f_at | Maltase | -2.3 |
| YCL030c/HIS4_at | Phosphoribosyl-AMP cyclohydrolase / phosphoribosyl-ATP pyrophosphohydrolase / histidinol dehydrogenase, second, third, and tenth | 2.4 |
| YCR059c/_at | Protein of unknown function, has similarity to mouse impact protein | 2.5 |
| YCR069w/SCC3_at | Cyclophilin (peptidylprolyl isomerase) of the endoplasmic reticulum membrane, homolog of ninaA | 2.4 |
| YCR070w/SCC3_at | Protein of unknown function | 2 |
| YCR073c/_at | SSK22; Map kinase kinase (MAPKKK) with strong similarity to Ssk2p, participates in the high-osmolality signal transduction pathway | 2.4 |
| YDL057w/_at | Protein of unknown function | 2.4 |
| YDL223c/_at | Protein of unknown function | 2.2 |
| YDR044W/HEM13_at | Coproporphyrinogen III oxidase, oxygen-repressed, sixth step in heme biosynthetic pathway | 2.8 |
| YDR261c/EXG2_at | Exo-beta-1,3-glucanase (beta-1,3-D-glucanglucanohydrolase), minor isoform | 2 |
| YDR488c/PALC11_at | Protein with similarity to rat dynein intermediate chain; requuireed in the absence of Cin8p, member of WD (WD-40) repeat family | -1.7 |
| YEL070w/_f_at | Protein with similarity to E. coli D-mannonate oxidoreductase (Yel070p and Ynr073p are identical proteins) | 3 |
| YER069w/ARG5,6_at | Acetylglutamate kinase and N-acetyl-gamma-glutamyl-phosphate reductase; catalyzes second and third steps of ornithine and arginine | 2.1 |
| YFL058W/THI5_f_at | Biosynthetic enzyme involved in primidine biosynthesis pathway above the hydroxymethyl-pyrimidine precurser leading to the hydroxymethyl-pyrimidine precurser leading to the | 2.2 |
| YFL059W/_f_at | SNZ3; Member of the stationary phase-induced gene family; other members include Snz1p and Snz2p | 2.1 |
| YFL061W/_f_at | Protein strongly induced after DNA-damage, has similarity to E. coli cyanamide hydratase (urea hydrolyase) (YFL061W and YNL335W | -3.2 |
| YFR017C/_at | Protein of unknown function | 2.1 |
| YFR018C/_at | Protein with similarity to human glutaminyl-peptide cyclotransferase | 2.1 |
| YFR023W/PES4_at | Suppressor of DNA polymerase epsilon mutation (PAB-like protein), contains 4 RNA recognitiion (RRM) domains | -3.1 |
| YGL081W/_at | Protein of unknown function | 2.8 |
| YGL157W/_at | Protein with weak similarity to tomato dihydroflavonol 4-reductase | 2.2 |
| YGL170C/_at | Protein with similarity to phosphoribulokinase precursor | -3.5 |

FIG. 5D

| Gene Name | Function | Fold Change |
|---|---|---|
| YGR014W/MSB2_at | Protein for which overproduction suppresses bud emergence defect of cdc24 mutant | 2.3 |
| YGR032W/GSC2_at | Component of beta-1,3-glucan synthase, probably functions as an alternate subunit with Fks1p with which it has strong similarity | 3.2 |
| YGR043C/_at | Protein with strong similarity to Tal1p | 2.2 |
| YGR161C/_at | Protein of unknown function, has phosphopantetheine attachment site | 2.4 |
| YGR166W/KRE11_at | Potential regulatory protein involved in synthesis of cell wall beta-1,6-glucan | 2 |
| YGR189C/_at | CRH1; Cell wall protein | 2 |
| YGR259C/_at | Protein of unknown function | 2 |
| YGR287C/_at | Protein with similarity to alpha-D-glucosidase (maltase) | ~2.2 |
| YGR292W/MAL1_f_at | MAL12; Alpha-glucosidase (maltase) of the MAL1 focus | 4.1 |
| YHL022c/SPO11_at | Catalytic subunit of the meiotic double strand break transesterase | ~5.9 |
| YHR214W-a/_f_at | Protein of unknown function | 2.8 |
| YIL006W/_at | Protein with similarity to Fix1p, Yel006p, and other members of the mitochondrial carrier (MCF) family | 2.4 |
| YIL080W/_f_at | Protein of unknown function | 2.2 |
| YIL082W-a/_ex2_f_at | Protein of unknown function | 2 |
| YIL099W/SGA1_at | Glucoamylase (glucan-alpha-1,4-glucosidase), sporulation-specific | 2.4 |
| YIL140W/SRO4_at | Membrane glycoprotein localized at site of bud emergence, required for axial budding pattern | 2.9 |
| YIL155C/GUT2_at | Mitochondrial FAD dependent glycerol-3-phosphate dehydrogenase | 3.9 |
| YIL169C/_at | Protein of unknown function | ~20.1 |
| YJL082W/_at | Protein of unknown function | 2.1 |
| YJL088W/ARG3_at | Ornithine carbamyltransferase, catalyzes the sixth step in the arginine biosynthesis pathway | 2.3 |
| YKL101W/HSL1_at | Serine/threonine protein kinase that genetically interacts with histone mutants | 2.4 |
| YKR013/PRY2_at | Protein expressed under starvation conditions | 3 |
| YLL012w/_at | Protein with similarity to human triacylglycerol lipase | 2.6 |
| YLR042c/_at | Protein of unknown function | 6.1 |
| YLR099c/_at | Protein of unknown function | 2.6 |
| YLR121c/_at | YPS4; Yaspin4, GPI-anchored aspartyl protease | 3.4 |
| YLR260W/_at | LCB5; Long chain base kinase, involved in biosynthesis of sphingolipid | 2.3 |
| YLR326W/_at | Protein of unknown function | 4 |
| YLR348C/_at | DIC1; Mitochondrial dicarboxylate transport protein, member of the mitochondrial carrier family | 2.6 |
| YMR103C/_at | Protein of unknown function, questionable orf | 2.7 |
| YMR104C/YPK2_at | Serine/threonine kinase with similarity to Ypk1p | ~2.7 |
| YMR199W/_at | Protein of unknown function | 3.5 |
| YMR199W/CLN1_at | G1/S-specific cyclin that interacts with Cdc28p protein kinase to control events at START | 2.4 |
| YMR305C/_at | SCW10; Protein with similarity to Bgl2p and other glucans | 2.3 |
| YNL138W/SRV2_at | Adenylate cyclase-associated protein (CAP) that may provide a link between growth signals and the cytoskeleton | 1.9 |
| YNL195C/_at | Protein of unknown function | 2.2 |
| YNL283C/_at | WSC2; Protein required for maintenance of cell wall integrity and for the stress response | 2 |
| YNL289W/PCL1_at | G1/S-specific cyclin that can interact with the Cdc28p-like kinase Pho85p | 4.7 |
| YNL300W/_at | Protein with weak similarity to Mid2p | 2.5 |
| YNL333W/_f_at | SN22; Member of the stationary phase-induced gene family which includes Snz1p and Snz3p | 2.2 |
| YNR033W/ABZ1_at | Para-aminobenzoate synthase | 2.1 |

FIG. 5E

| Gene Name | Function | Fold Change |
|---|---|---|
| YNR057C/B104_at | Dethiobiotin synthase, component of the biotin biosynthesis pathway | 2 |
| YNR058W/B103_at | DAPA aminotransferase, component of the biotin biosynthesis pathway | 2.6 |
| YNR066C/_at | Protein with similarity to Pep1p | -2.1 |
| YOL007C/_at | CSI2; Protein involved in chitin synthesis | 3.2 |
| YOL047C/_ex1_at | Protein of unknown function | -2.2 |
| YOL113W/_at | SKM1; Serine/threonine protein kinase with similarity to Ste20p and Cla4p | 2.7 |
| YOL155C/_at | Protein with similarity to S. cerevisiae glucan 1,4-alpha-glucosidase | 2.2 |
| YOR003W/YSP3_at | Subtilisin-like protease III | 2 |
| YOR114W/_at | Protein of unknown function | 2.3 |
| YOR248W/_i_at | Protein of unknown function | 2.3 |
| YOR343C/_at | Protein of unknown function | -3.3 |
| YOR393W/ERR1_f_at | Enolase-related subtelomeric sequence (see R316) | -2.5 |
| YPL111W/CAR1_at | Arginase; catalyzes the first step in arginine degradation and acts as an allosteric regulator of ornithine carbamyltransferase | 2.4 |
| YPL189W/_at | Member of the major facilitator superfamily (MFS); protein of unknown function | -2.2 |
| YPL256C/CLN2_at | G1/S-specific cyclin; interacts with Cdc28p protein kinase to control events at START | 3.3 |
| YPL280W/_f_at | Protein of unknown function | 3.1 |
| YPR005C/HAL1_at | Protein involved in ion homeostasis | 2.2 |

IV. Gene transcription decreased after 120 minute exposure to 500 nM 4-amino-1-(tert-butyl)-3-(1'-naphthylmethyl)pyrazolo[3,4-d]pyrimidine

| Gene Name | Function | Fold Change |
|---|---|---|
| YAL061W/_at | Fun503;16 PM Protein with similarity to alcohol/sorbitol dehydrogenase; member of the zinc-containing alcohol dehydrogenase family | -1.3 |
| YAR018C/KIN3_at | Serine/threonine protein kinase; null mutant has no phenotype | -1.8 |
| YAR071W/PHO11_f_at | Acid phosphatase, secreted | -4.9 |
| YBL002w/HT82_at | Histone H2B | -4.6 |
| YBL003c/HTA2_at | Histone H2A | -2.2 |
| YBR010w/HHT1_at | Histone H3 | -2.1 |
| YBR054w/YRO2_at | Protein with similarity to heat shock protein hsp30p | -7.8 |
| YBR067c/TIP1_at | Cold- and heat-shock induced mannoprotein of the cell wall; member of the PAU1 family | -2.2 |
| YBR007c/_at | Protein of unknown function | -2.6 |
| YBR092c/PHO3_at | Acid phosphatase, constitutive, thiamine-binding protein of the periplasmic space | -21.5 |
| YBR093c/PHO5_at | Acid phosphatase, repressable, requires glycosylation for activity | -10.6 |
| YBR158w/_at | Protein required for optimal growth and germination rate | -4.7 |
| YBR244w/_at | Protein with similarity to glutathione peroxidase | -3.0 |
| YCR024c-a/PMP1_f_at | Plasma membrane proteolipid associated with Pma1p | -2.1 |
| YDL179w/_at | Pcl9; Cyclin, associates with Pho85p | -4.9 |
| YDR033w/_at | Protein with similarity to Yro2p | -13.6 |
| YDR055w/_at | Pst1; Protein with similarity to members of the Sps2p-Ecm33p-Ycl048p family | -3.5 |
| YDR089w/_at | Protein of unknown function; has leucine zipper | -1.8 |
| YDR146c/SW15_at | Transcription factor that controls cell cycle-specific transcription of HO | -3.1 |
| YDR357C/_at | Protein of unknown function | -2.4 |
| YDR461w/MFA1_at | mating pheromone a-factor; exported from cell by Ste6p | -3.2 |

FIG. 5F

| Gene Name | Function | Fold Change |
|---|---|---|
| YEL032w/MCM3_at | Protein that acts at ARS elements to initiate replication; member of the MCM/P1 family | -2.6 |
| YEL075c/_f_at | Protein with similarity to other subtelomerically-encoded proteins including Yhl049p, Yil177p, and Yjl225p | -2.1 |
| YER067w/_at | Protein of unknown function | -5.5 |
| YER124c/_at | Protein of unknown function | -9.8 |
| YER148wM_at | SPT15; TATA-binding component of RNA polymerases I, II and III; part of initiation factors TFIID and TFIIB | -2 |
| YER150w/_at | SPI1; Protein induced in stationary phase, has similarity to Sed1p | -2.6 |
| YFL014W/HSP12_at | Heat shock protein of 12kDa, induced by heat, osmostress, oxidative stress and stationary phase | -2.1 |
| YFL026W/STE2_at | Pheromone alpha-factor receptor; has seven transmembrane segments | -2.5 |
| YFL064C/_f_at | Protein with similarity to other subtelomerically-encoded proteins including Yhl049p, Yil177p, Yjl225p, Yer189p, Yel075p, and | -2.1 |
| YFR053C/HXK1_at | Hexokinase I, converts hexoses to hexose phosphates in glycolysis; repressed by glucose | -2 |
| YGL021W/ALK1_at | DNA damage-responsive protein | -3.5 |
| YGL028C/_at | SCW11; Putative cell wall protein with similarity to Scw10p | -16.4 |
| YGL032C/AGA2_at | a-Agglutinin binding subunit | -6.5 |
| YGL101W/_at | Protein of unknown function | -2 |
| YGL116W/CDC20_at | Protein required for microtubule function at mitosis; member of WD (WD-40) repeat family | -4.1 |
| YGR041W/_at | BUD9; Protein required for bipolar budding; mutant diploid strains bud only at distal pole | -2.2 |
| YGR044C/RME1_at | Zinc-finger transcription factor that represses meiosis in non-a/alpha cells | -3.1 |
| YGR092W/DBF2_at | Serine/threonine protein kinase related to Dbf20p, required for events in anaphase/telophase | -2.6 |
| YGR108W/CLB1_at | G2/M-phase-specific cyclin | -2.3 |
| YGR143W/SKN1_at | Glucan synthase subunit involved in synthesis of beta-1,6-glucan | -2.5 |
| YGR177C/ATF2_at | Sterol O-acetyltransferase; acetylates certain toxic steroids such as pregnenolone to render them excretable | -5.1 |
| YGR230W/_at | BNS1; Protein with similarity to Spo12p, able to partially suppress requirement for Spo12p in meiosis | -3.7 |
| YGR260W/_at | Protein with similarity to Dal5p and member of the allantoate permease family of the major facilitator superfamily | -2 |
| YHL028W/_at | WSC4; Protein required secretory protein translocation, for maintenance of cell wall integrity and for the stress response | -6.9 |
| YHR005c/GPA1_at | Guanine nucleotide-binding protein alpha subunit of the pheromone response pathway | -2.2 |
| YHR023w/MYO1_at | Myosin heavy chain (myosin II), coiled-coil protein involved in septation and cell wall organization | -3 |
| YHR143W/_at | Protein of unknown function | -41.2 |
| YHR152w/SPO12_at | Sporulation protein required for chromosome division in meiosis I | -2.4 |
| YHR215w/PHO12_f_at | Acid phosphatase, secreted | -5.9 |
| YHR218W/_ex1_f_at | Protein with near identity to subtelomerically-encoded proteins including Yhr219p and Yfl065p, possible pseudogene | -3 |
| YIL001W/_at | Protein of unknown function | -2 |
| YIL009W/FAA3_at | Acyl-CoA synthase (long-chain fatty acid CoA ligase); activities endogenous but not imported fatty acids | -4.7 |
| YIL015W/BAR1_at | Secreted pepsin-like protease; degrades alpha-factor | -5.1 |
| YIL092W/_at | Protein of unknown function | -2 |
| YIL106W/MOB1_at | Protein required for completion of mitosis and maintenance of ploidy | -2.3 |
| YIL119C/RPI1_at | Negative regulator of ras-cAMP pathway, downregulates noemal but not mutant ras function | -2.7 |
| YIL158W/_at | Protein with similarity to Ykkr100p | -3.1 |
| YIL167W/_at | Serine dehydratase, converts serine to pyruvate and amonia for gluconeogenesis | -3.8 |
| YIL168W/SDL1_at | Serine dehydratase, converts serine to pyruvate and amonia for gluconeogenesis | -4.7 |
| YJL044C/GYP6_at | GTPase-activating protein for Ypt6p | -2.5 |
| YJL048C/_at | Protein of unknown function | -2 |

FIG. 5G

| Gene Name | Function | Fold Change |
|---|---|---|
| YJL051W/_at | Protein of unknown function | -4 |
| YJL078C/PRY3_at | Protein with similarity to plant pathenogenesis-related proteins | -2.7 |
| YJL079C/PRY1_at | Protein expressed under starvation conditions | -3.2 |
| YJL157C/FAR1_at | Inhibitor of Cdc28p-Cln2p kinase complexes involved in cell cycle arrest for mating | -20.4 |
| YJL159W/_at | Secreted O-glycosylated protein required for tolerance to heat shock; member of Pir1/Hsp150p/pir3 family of proteins with variable | -2.2 |
| YJL170C/_at | ASG7; Protein expressed only in cells of mating type a | -2.7 |
| YJL196C/_at | ELO1; Fatty acid elongation protein involved in elongation of tetradecanoic acid (14:0) to hexadecanoic acid (16:0) | -2 |
| YKL001C/MET14_at | Adenosine-5'-phosphosulfate 3' phosphotransferase; (adenylylsulfate kinase), part of the sulfate assimilation pathway | -2.9 |
| YKL164C/PIR1_at | Protein required for tolerance to heat shock, member of the Pir1p/Hsp150p/Pir3p family | -3.7 |
| YKL209C/STE6_at | membrane transporter responsible for export of "a" factor mating pheromone; member of ATP-binding cassette (ABC) superfamily | -5.8 |
| YKR042W/_at | UTH1; Protein involved in the aging process; mutants have longer lifespan and better viability upon starvation | -2.5 |
| YLR254C/_at | Protein of unknown function | -4.2 |
| YLR258W/GSY2_at | UDP-glucose-starch glucosyltransferase (glycogen synthetase) isoform 2 | -2.4 |
| YLR286C/CTS1_at | Endochitinase | -28.4 |
| YML052W/_at | SUR7; Protein of unknown function; overproduction suppresses the rvs167 mutation | -2.5 |
| YML064C/TEM1_at | GTP-binding protein of the ras superfamily; involved in termination of M-phase | -2.1 |
| YML119W/_at | Protein of unknown function | -4.1 |
| YMR031C/_at | Protein of unknown function, has potential coiled-coil region | -2.0 |
| YMR090W/_at | Protein with similarity to malate dehydrogenases | -2 |
| YNL046W/_at | Protein of unknown function | -5.7 |
| YNL058C/_at | Protein of unknown function | -3.1 |
| YNL066W/_at | SUN4; Protein involved in the aging process | -4.1 |
| YNL145W/MFA2_at | Mating pheromone a-factor; exported from cell by Ste6p | -6.9 |
| YNL160W/YGP1_at | Secreted glycoprotein produced in response to nutrient limitation | -5.5 |
| YNL327W/_at | EGT2; Cell-cycle regulation protein; may be involved in the correct timing of cell separation after cytokinesis | -28.3 |
| YNR067C/_at | Protein of unknown function | -19.4 |
| YOR025W/HST3_at | Protein with similarity to Sir2p | -4.1 |
| YOR066W/_at | Protein of unknown function | -3.7 |
| YOR229W/_at | WTM2; Transcriptional modulator protein involved in meiotic regulation and silencing; member of WD (WD-40) repeat family | -2 |
| YOR264W/_at | Protein of unknown function | -4.7 |
| YOR315W/_at | Protein of unknown function | -2.2 |
| YOR344C/TYE7_at | Basic helix-loop=helix transcription factor that can suppress the Gcr1p requirement for glycolytic gene expression | -2 |
| YOR348C/PUT4-at | Proline permease; required for high-affinity proline transport | -3.2 |
| YPL158C/_at | Protein of unknown function | -4.6 |
| YPL242C/_at | IQG1; Protein involved in cytokinesis; has similarity to mammalian IQGAP peoteins | -2.1 |
| YPR119W/_at | CLB2; G2/M-phase-specific cyclin | -4.1 |
| YPR149W/NCE2_at | Protein involved in non-classical protein export pathway for proteins that lack standard secretory signal sequences | -2 |
| YPR160W/GPH1_at | Glycogen phosphorylase; releases alpha-D-glucose-1-phosphate from glycogen | -2.9 |

METHODS FOR IDENTIFYING CELLULAR RESPONSES ATTRIBUTABLE TO SIGNALING MOLECULE INHIBITION AND INHIBITORS THEREOF

CROSS-REFERENCE TO RELATED APPLICATION

This application claims priority to Provisional application Serial No. 60/145,422, filed Jul. 23, 1999, incorporated herein by reference in its entirety.

FIELD OF THE INVENTION

The present invention provides a method for the identification of a pattern of changes in cellular responses induced by the selective inhibition of a signaling molecule, and methods for identifying selective inhibitors thereof.

BACKGROUND OF THE INVENTION

Cell-to-cell communications in a multicellular organism are fast and allow cells to respond to one another in diverse and complex ways. Typically, the intracellular signals are molecules called "ligands," and a given ligand can bind to a particular type of receptor on the surface of those cells that are to receive that signal, but this simple ligand binding alone is not enough to provide for the complex responses that the receiving cells may need to make. Cells therefore amplify and add complexity to this signal through complex, often cascading, mechanisms leading to the rapid modulation of catalytic activities inside the cell, which in turn can produce complex, and sometimes dramatic, intracellular responses. This process as a whole, from initial ligand binding to completion of the intracellular response, is called "signal transduction."

Signal transduction is often accomplished by the activation of intracellular enzymes that can act upon other enzymes and change their catalytic activity. This may lead to increases or decreases in the activity certain metabolic pathways, or may lead to even large intracellular changes, for example, the initiation of specific patterns of gene expression. The ability of one enzyme to alter the activity of other enzymes generally indicates that the enzyme is involved in cellular signal transduction.

The most common covalent modification used in signal transduction processes is phosphorylation, which results in the alteration of the activity of those enzymes which become phosphorylated. This phosphorylation is catalyzed by enzymes known as ATP-dependent phosphotransferases which are often simply referred to as "kinases." These include, among others, protein kinases, lipid kinases, inositol kinases, non-classical protein kinases, histidine kinases, aspartyl kinases, nucleoside kinases, and polynucleotide kinases.

Several key features of such kinases make them ideally suited as signaling proteins. One is that they often have overlapping target substrate specificities, which allows "cross-talk" among different signaling pathways, thus allowing for the integration of different signals (1). This is thought to be a result of the need for each kinase to phosphorylate several substrates before a response is elicited, which in turn provides for many types of diverse signaling outcomes. For example, a given kinase may in one instance transmit a growth inhibitory signal and in another instance transmit a growth promoting signal, depending on the structure of the extracellular ligand that has bound to the cell surface (2).

A second key feature is that the kinases are organized into several modular functional regions, or "domains" (3). One domain known as "SH3" is a proline-rich region of 55–70 amino acids in length, and another, known as "SH2," is a phosphotyrosine-binding region of about 100 amino acids in length. These two domains are believed to be involved in recognizing and binding to the protein substrates. The third domain, "SH1," is comprised of about 270 amino acids, and is the domain which is responsible for catalysis. It also contains the binding site for the nucleoside triphosphate which is used as energy source and phosphate donor (3). Other domains, including myristylation and palmitylation sites, along with SH2 and SH3, are responsible for assembling multiprotein complexes which guide the catalytic domain to the correct targets (3,22,23). Molecular recognition by the various domains has been studied using by x-ray diffraction and by using NMR methods (24–28).

These domains appear to have been mixed and matched through evolution to produce the large protein kinase "family." As many as 2000 kinases are thought to be encoded in the mammalian genome (4), and over 250 kinases have already been identified. The large number of kinases and the large number of phosphorylation-modulated enzymes that are known to exist inside cells allow for rapid signal amplification and multiple points of regulation.

A third key feature of the kinases is their speed. The kinetics of phosphorylation and dephosphorylation is extremely rapid in many cells (on a millisecond time scale), providing for rapid responses and short recovery times, which in turn makes repeated signal transmission possible (5).

These features of the kinases have apparently led them to be involved in a vast array of different intracellular signal transduction mechanisms. For example, growth factors, transcription factors, hormones, cell cycle regulatory proteins, and many other classes of cellular regulators utilize tyrosine kinases in their signaling cascades (12,13). Tyrosine kinases catalytically attach a phosphate to one or more tyrosine residues on their protein substrates. The tyrosine kinases include proteins with many diverse functions including the cell cycle control element c-abl (14–16), epidermal growth factor receptor which contains a cytoplasmic tyrosine kinase domain (12),c-src, a non-receptor tyrosine kinase involved in many immune cell functions (13), and Tyk2, a cytoplasmic tyrosine kinase which is involved in phosphorylation of the p91 protein which is translocated to the nucleus upon receptor stimulation and functions as a transcription factor (17).

The serine/threonine kinases make up much if not all of the remainder of the kinase family; these catalytically phosphorylate serine and threonine residues in their protein substrates, and they have similarly diverse roles. They share homology in the 270 amino acid catalytic domain with tyrosine kinases. As such, although the discussion which follows focuses more particularly on the tyrosine kinases, that discussion is generally applicable to the serine/threonine kinases as well. An example of a protein kinase in yeast is CDC28. This is the major protein kinase in yeast which controls the cell cycle.

One important avenue for deciphering the role and understanding the function of enzymes, both in vitro and in vivo, is the use of specific enzyme inhibitors. If one or more compound can be found that will inhibit the enzyme, the inhibitor can be used to modulate the enzyme's activity, and the effects of that decrease can be observed. Such approaches have been instrumental in deciphering many of the pathways of intermediary metabolism, and have also been important in learning about enzyme kinetics and determining catalytic mechanisms.

In addition, such inhibitors are among the most important pharmaceutical compounds known. For example, aspirin (acetylsalicylic acid) is such an inhibitor. It inhibits an enzyme that catalyzes the first step in prostaglandin synthesis, thus inhibiting the formation of prostaglandins, which are involved in producing pain (72). Traditional drug discovery can be characterized as the design and modification of compounds designed specifically to bind to and inactivate a disease-causing protein; the relative success of such an effort depends upon the selectivity of the drug for the target protein and its lack of inhibition of non-disease associated enzymes with similar enzyme activities.

Such approaches would appear to be promising ways to develop treatments for cancer, since many human cancers are caused by dysregulation of a normal protein (e.g., when a proto-oncogene is converted to an oncogene through a gene translocation). And since kinases are key regulators, they have turned out to be very common proto-oncogenes, and thus ideal drug design targets. The process of designing selective inhibitors is relatively simple in cases where few similar enzymes are present in the target organism, for example in cases where inhibitors of a protein unique to bacteria can be targeted. But unfortunately, the similarities between the kinases and their large number has frustrated the discovery and design of specific inhibitors, and has blocked most hopes of developing specific pharmaceutical treatments aimed at the proto-oncogene level. It is expected that the vast majority of candidate inhibitors will inhibit multiple kinases, even though they may have initially been identified as inhibiting a particular, purified kinase.

This is not to say, however, that inhibitors with at least some degree of kinase-specificity cannot be found. Several natural products have been identified which are relatively specific for particular kinase families, but attempts to derive general rules about kinase inhibition based on these has failed. Furthermore, as the following examples show, specificity in most cases is quite limited. For example, the compound damnacanthal was reported to be a "highly potent, selective inhibitor" of the kinase p56lck (73); this compound has an 50% inhibitory concentration ($IC_{50}$) for that kinase which is almost seven times lower than for the kinase src (the $IC_{50}$ is the concentration of inhibitor which must be added to reduce catalytic activity by 50%). The compound PPI has a binding affinity for the kinase lck which is very strong ($IC_{50}$=0.005 $\mu$M); but unfortunately, the inhibition of other kinases of the src family is very similar. It inhibits the kinase fyn with an almost identical $IC_{50}$, 0.006 $\mu$M, and has only about a 4-fold higher $IC_{50}$ for the kinase hck ($IC_{50}$=0.020 $\mu$M). The compound CGP 57148 has been reported to be "semi-selective" for the kinases abl ($IC_{50}$= 0.025 $\mu$M) and PDGFR ($IC_{50}$=0.030 $\mu$M)(74). Nevertheless, considering the vast number of kinases and their relative cellular importance, and also considering that the above-described inhibitors have only been reported in the last two years, it appears that success in discovering or designing selective kinase inhibitors has been limited.

These difficulties described above have implications well beyond the mere frustration of scientists; they have frustrated efforts to decipher the kinase cascades and the function of individual kinases in those cascades and other cellular mechanisms. Such an understanding of kinase activity and function may be essential before certain human diseases can be effectively treated, prevented or cured. For example, it has been known for over 30 years that the oncogene bcr-abl is a protein kinase that is responsible for chronic myelogenous leukemia; but the physiological substrates that it acts upon to cause oncogenesis, which may be important drug design targets, have yet to be definitively identified (11). On the bright side, despite this shortcoming, the above-described inhibitor CGP 57148 is reportedly now undergoing clinical trials for use in treating myelogenous leukemia, even though the substrates it may block phosphorylation of in vivo are not known.

The medical significance of these difficulties is further illustrated by the Rous sarcoma virus (RSV), which has become an important model system for studying the role of kinases in oncogenesis. RSV transformation of fibroblasts is controlled by a single viral gene product, the protein tyrosine kinase v-src (32). It is the rapid time course and the dramatic morphological changes during RSV fibroblast transformation that have made RSV a paradigm for studies of oncogene activity in all cells. The origin (33), regulation (3,8,34,35), and structure (25,27,36) of v-Src have been extensively studied and are well understood (8,37,38). But central questions about this intensely studied kinase remains unanswered: what are its direct cellular substrates? Does inhibition of its catalytic activity effectively inhibit, or even reverse, transformation? Would such inhibition be an effective therapy for or prophylactic against RSV transformation? Unfortunately, as discussed above, the answers to these questions are not forthcoming, largely because the number of cellular kinases is enormous (it is estimated that 2% of the mammalian genome encodes protein kinases (4)) and because tyrosine kinases display overlapping substrate specificities (8,39) and share catalytic domains, making the design of specific inhibitors difficult.

The expression of v-Src in fibroblasts results in the tyrosine phosphorylation of over 50 cellular proteins (37). These same substrates are also phosphorylated by other kinases in untransformed fibroblasts (40). Even sophisticated biochemical and genetic techniques, including anti-phosphotyrosine protein blots of transformed fibroblasts, transfection of fibroblasts with transformation-defective v-Src mutants, temperature-sensitive v-Src mutants, gene knock-out studies of cellular Src, host-range dependent Src mutants, anti-v-Src immunoprecipitation, and use of kinase-specific inhibitors, have not led to the unambiguous identification of v-Src's direct substrates (see reference (38) for a comprehensive review). But this situation is not unique; in fact, the direct substrates for the majority of cellular kinases remain unidentified (8). Furthermore, as discussed above, there also are few compounds known to selectively inhibit individual kinases, or even groups of related kinases.

Certain protein kinases because of their central importance in cell division have become very active drug targets. One such kinase is cyclin dependent kinase 2 (the yeast homolog is CDC28). CDK2 activity is required to proceed through the cell cycle. Therefore, diseases which are caused by abnormal growth of cells or tissues could be blocked if the progression through the cell cycle could be blocked by inhibition of CDK2 in these cells. Examples of such diseases include: tumor growth, restenosis and atherosclerosis, glomerulonephritis, psoriasis, and Alzheimer's disease. The basis for disease treatment is that disease related cells must divide faster than "normal" cells and thus will be more sensitive to potent agents which block cell cycle progression.

In particular, cell cycle control kinases are important targets for anti-cancer therapy based on the identification of the role of these kinases in controlling cellular proliferation. One such example is the yeast homolog CDC28 of such a cell cycle control kinase.

From the forgoing, it is clear that there has been a long felt but unsatisfied need for ways to identify inhibitors of specific signaling molecules, protein kinases being an example. More particularly, a need exists for a method for identifying specific inhibitors without the arduous task of expression, purification, and assay of the ever-growing number of described signaling molecules, a number that is increasing rapidly. Over 1000 kinases are known. The need exists for method for identifying specific inhibitors of individual kinases or kinase families, which could be used to identify protein substrates (by looking for which proteins are not phosphorylated or are more weakly phosphorylated in the presence of the inhibitor), to study the biochemical and phenotypic effects of rapidly down-regulating a given kinase's activity, for use as drugs to treat kinase-mediated diseases, and to confirm that tedious efforts to design or develop more traditional inhibitor drugs would be worthwhile.

It is towards the development of a method for identifying a pattern of cellular responses resulting from the selective inhibition of a signaling molecule, and methods of using the pattern for identifying selective inhibitors of the signaling molecule, that the present invention is directed.

The citation of any reference herein should not be construed as an admission that such reference is available as "Prior Art" to the instant application.

DEFINITIONS

The following terms have the definitions as used herein:

"Signaling Molecule" is a molecule involved in transmitting information about the external environment surrounding a cell: e.g., a receptor for a growth factor, or an enzyme which is activated after the growth factor binds to the receptor.

"Cellular Response" is any quantitatively or qualitatively measurable change of a unitary or complex event in a cell, for example, as a consequence of exposure to a stimulant, an inhibitor, change in the environment, or change over time. Such a cellular response may be either decreased, increased, or unchanged, compared to that which would occur in the absence of such exposure, such as increased, decreased or unchanged levels of gene transcription, protein expression, metabolism, etc. over a particular time period, or as a consequence of a perturbation to the cell, whether environmental, chemical, or otherwise. The particular cellular response(s) need not be further characterized, for example, as to specific gene transcripts or proteins.

"Pattern of Cellular Responses" is a composite representation of the changes or lack of changes in a plurality of cellular responses characteristic of or attributable to the inhibition of a particular signaling molecule in a cell.

"Altered" refers to a change in the level of a cellular response. This change may be but is not limited to increased, decreased, disappearance, or appearance.

"Wild type" refers to the naturally occurring (non-mutated) form of the signaling molecule under consideration. The wild-type form of the signaling molecule may be provided in a host cell, referred to herein as the wild-type cell. This cell may or may not be the natural cell in which the signaling molecule is present.

"Mutant" refers to an form of the signaling molecule containing one or more changes to the protein sequence of the wild-type sequence. A functionally silent mutation refers to a mutation which does not alter the phenotype of the cell, i.e., the signaling molecule for which the mutant gene encodes retains its function as compared to the wild-type molecule. The mutant form of the molecule is provided in a host cell, referred to herein as the mutant cell.

SUMMARY OF THE INVENTION

The present invention provides methods by which the pattern of cellular responses by the selective inhibition of a signaling molecule may be determined, and using this pattern, selective inhibitors of the signaling molecule may be identified. It has been discovered by the inventors herein that a characteristic pattern of cellular responses that is determined from the selective inhibition of a functional, silent mutation of a particular signaling molecule, is a pattern that represents the cellular responses resulting from the inhibition of the wild-type signaling molecule. Thus, a pattern of cellular responses identified for a particular signaling molecule may be used to identify selective inhibitors by determining whether the characteristic pattern results from the candidate inhibitor; furthermore, the pattern of effects of an inhibitor may be used to identify the signaling molecule being inhibited.

In its broadest aspect, the present invention is directed to patterns of cellular responses attributable to the selective inhibition of a wild-type form of a preselected signaling molecule, wherein the patterns comprise changes in the cellular responses attributable to selective inhibition of a mutant form of the preselected signaling molecule by a selective inhibitor of the mutant form of the preselected signaling molecule. The invention is directed further to the use of the aforementioned patterns to identify selective inhibitors of wild-type forms of signaling molecules.

In another aspect, the present invention involves methods for identifying a pattern of cellular responses attributable to the selective inhibition of a wild-type form of a preselected signaling molecule comprising the steps of:

A method for identifying a pattern of cellular responses attributable to the selective inhibition of a wild-type form of a preselected signaling molecule comprising the steps of:

(a) providing mutant cells which have a mutant signaling molecule in place of or coexisting with the wild-type signaling molecule;

(b) providing a selective inhibitor of the mutant signaling molecule;

(c) identifying cellular responses exhibited by the mutant cells before and after exposure to the mutant inhibitor, optionally in addition to identifying the exhibited cellular responses selected from
   i) wild-type cells unexposed to said mutant inhibitor,
   ii) wild-type cells after exposure to said mutant inhibitor, or
   iii) the combination of i) and ii) above; and (d) comparing said cellular responses obtained in step (c) above to identify a pattern of cellular responses attributable to the selective inhibition of said wild-type preselected signaling molecule wherein the pattern comprises the cellular responses attributable to selective inhibition of the mutant signaling molecule in the mutant cells.

In a further aspect, the present invention involves methods for identifying a pattern of cellular responses attributable to the selective inhibition of a wild-type form of a preselected signaling molecule comprising the steps of:

(a) providing wild-type cells which have a wild-type signaling molecule, (b) providing mutant cells which have a mutant signaling molecule in place of or coexisting with the wild-type signaling molecule;

(c) providing a selective inhibitor of the mutant signaling molecule;

(d) identifying cellular responses exhibited by wild-type cells that are not exposed to the mutant inhibitor;

(e) identifying cellular responses exhibited by wild-type cells after exposure to the mutant inhibitor;

(f) identifying cellular responses exhibited by the mutant cells which are not treated with the mutant inhibitor;

(g) identifying cellular responses exhibited by the mutant cells after exposure to the mutant inhibitor; and (h) comparing said cellular responses in steps (d), (e), (f) and (g) to identify a pattern of cellular responses attributable to the selective inhibition of said wild-type preselected signaling molecule wherein said pattern comprises the cellular responses attributable to selective inhibition of said mutant signaling molecule in said mutant cells.

In a further embodiment, the wild-type and mutant cells in either of the foregoing methods may be exposed to a stimulant in order to induce cellular responses. Non-limiting examples of such stimulants include hormones, cytokines, growth factors, heat, cold, light, metal ions, osmolarity changes, contact, heterologous cells, pressure, oxidative stress, natural products, plant extracts, marine organisms, synthetic compounds, combinatorial organic libraries, peptide libraries, organ tissue explants, or via cell transfer into animals, among other factors, which will be related to the particular cell type.

The foregoing method is applicable to a wide variety of signaling molecules. By way of non-limiting examples, such molecules as transcription factors, ATP-dependent phosphotransferases, myosin motors, histone acetyl transferases, ion channels, farnesyl transferases, ligand gated channels, metabolic enzymes, natural product targets, the proteosome, ubiquitin pathway enzymes, complement system enzymes, proteases, intracellular stores of ions, vesicle trafficking enzymes, G-protein coupled receptors, proteases, and other signal transduction molecules are applicable to the present invention. In a preferred embodiment, the signaling molecule is an ATP-dependent phosphotransferase, such as a protein kinase, lipid kinase, inositol kinase, non-classical protein kinase, histidine kinase, aspartyl kinase, nucleoside kinase, or polynucleotide kinase. Non-limiting examples of protein kinases include those in groups known AGCs, calmodulin dependent protein kinases, CMGCs, protein tyrosine kinases, or other protein kinases. In a preferred embodiment, the protein kinase is CDC28 in yeast or v-src and cdk2 in humans.

The cellular responses identified in the foregoing method include any quantitatively or qualitatively measurable appearance, change, or disappearance of a parameter such as but not limited to gene transcription, protein expression, metabolic alteration, morphologic alteration, lipid alteration, growth alteration, cell shape change, cytoskeletal reorganization, protein translocation, protein relocalization, metal ion influx, metal ion efflux, change in osmolarity, receptor expression on the cell surface, receptor clustering, receptor desensitization, protein glycosylation, protein destruction, protein phosphorylation or other protein post-translational modification. The pattern of cellular changes may be a single or a plurality of changes, for example, a morphological change or the expression of a particular protein or mRNA. The pattern may be a plurality of responses, such as changes in a number of individual gene transcription products, perhaps hundreds to thousands; a plurality of proteins expressed, the levels of various intra-cellular metabolites of secreted products; the lipid makeup of the cell membrane, and so forth. These responses may be measured by known techniques applicable to the particular type of change. For example, changes in gene transcription may be measured using DNA chip array technology, cDNA array techniques on glass or nitrocellulose filters, oligonucleotide arrays on various solid supports, TAQman assay, quantitative PCR, competitive PCR, and differential display. Certain of these techniques may be better applicable to measuring a large number of responses, such as the DNA chip array technology for a large number of individual mRNA transcripts. By way of another example, a large number of expressed proteins may be measured using differential display, 2-D protein gel electrophoresis, mass spectroscopy, high-throughput mass spectroscopy, massively parallel protein identification technologies such as those based on monoclonal or polyclonal antibody recognition, RNA or DNA polymers which recognize various proteins, such RNA or DNA molecules could be produced from so-called in vitro evolution experiments, high-throughput confocal microscopy, X-ray diffraction, nuclear magnetic resonance spectroscopy, resonance Raman spectroscopy, capillary electrophoresis, and so forth.

The wild-type cells may be derived from any organism. This includes eukaryotic or prokaryotic cells. Eukaryotic cells include for example plant cells, animal cells such as mammalian, including human cells, and protistan cells including yeast, protozoans, and other eukaryotic microorganisms. Prokaryotic cells include bacteria, blue-green bacteria, including members of the Archaebacteria and eubacteria. The wild-type cells may be hosts for a signaling molecule from another species or kingdom.

The mutant cells with the mutant form of the signaling molecule may be prepared by any one of a number of methods known to the skilled artisan. For example, the mutant cells may be prepared by gene knock-in technology; or by mating or fusion between an organism or cell lacking the wild-type kinase and an organism or cell which contains both the wild type and the mutant kinase gene, followed by screening the progeny or resultant fusions for those which only have the mutant kinase gene and lack the wild-type kinase gene mutation. Furthermore, by way of non-limiting example, the methods described in copending application Ser. No. PCT/US98/02522 (published as WO 98/35048), incorporated herein by reference, may be used. The mutant signaling molecule may be of origin from any species or kingdom, and provided in any suitable host cell or any species or kingdom, to provide a mutant cell with the mutant signaling molecule suitable for use for the methods herein.

Selective inhibitors of the mutant signaling molecule may be identified and prepared by any of a number of methods known to the skilled artisan. Furthermore, by way of non-limiting example, the methods described in copending application Ser. No. PCT/US98/02522 (published as WO 98/35048), and in copending application Serial No. 60/115, 340, incorporated herein by reference, may be used. By way of non-limiting example, the inhibitor 4-amino-1-(tert-butyl)-3-(1'-naphthylmethyl)(tert-butyl)-3-(1'-naphthylmethyl)pyrazolo[3,4-d]pyrimidine is useful for the practice of the present invention.

For example, the pairs of wild type and mutant genes that may be used in the method of the present invention include but are not limited to CDC28 and CDC28 F88G, v-Src and v-Src 1338G, c-AMP dependent kinase (PKA) and PKA M120G or PKA M120A, p38 and p38 T106A or p38 T106G, Raf and Raf (V420A) or Raf (V420G), and the insulin receptor kinase (IRK) IRK(V1075A) or IRK (V1075G).

By way of example, a signaling molecule that may be selected to identify the characteristic pattern of cellular response to its inhibition in accordance with the present invention may be the yeast protein kinase CDC28, the mutant cells known as CDC28 expressing a mutant form of CDC28 referred to as CDC28 F88G, the selective inhibitor of the mutant inhibitor is 4-amino-1-(tert-butyl)-3-(1'-naphthylmethyl)pyrazolo[3,4-d]pyrimidine, and the cellular responses are gene transcription products. The gene transcription products are measured using DNA chip array technology.

In a further aspect of the present invention, the aforementioned method comprising the exposing the wild-type cells and the mutant cells to a non-specific inhibitor, and the pattern of cellular responses additionally comprising cellular responses which are altered or unaltered by the non-specific inhibitor. Non-limiting examples of non-specific inhibitors include 4-amino-1-tert-butyl-3-(p-methylphenyl)pyrazolo [3,4-d]pyrimidine, genestein, quercetin, K252a, staurosporine, adenosine, olomoucine, SKB 203580, damnacanthal, tyrphostins, erbstatin, piceatannol, lavendustin A, and radicicol.

In another broad aspect of the present invention, methods are provided for identifying a selective inhibitor of a wild-type form of a preselected signaling molecule. The method comprises the steps of first identifying a pattern of cellular responses attributable to the selective inhibition of a wild-type form of the preselected signaling molecule in accordance with the above-described methods; exposing wild-type cells to a candidate selective inhibitor of the wild-type form of the signaling molecule; identifying the effect of the candidate inhibitor on the pattern of cellular responses in the wild-type cell; and identifying a selective inhibitor as that which matches or resembles the pattern. In a further aspect, the wild-type cells are additionally exposed to a stimulant to induce the cellular responses, as described above.

These and other aspects of the present invention will be better appreciated by reference to the following drawings and Detailed Description.

BRIEF DESCRIPTION OF THE DRAWINGS

FIG. 1 depicts the non-specific drug effects at 30 and 120 minutes of 500 nM 4-amino-1-(tert-butyl)-3-(1'-naphthylmethyl)pyrazolo [3,4-d]pyrimidine on wild-type yeast cells with CDC28, using DNA chip array methods to monitor the transcription of 6200 genes. FIG. 1A is a schematic drawing of CDC28 alone and with 4-amino-1-(tert-butyl)-3-(1'-naphthylmethyl)pyrazolo[3,4-$d$] pyrimidine. FIG. 1B. After 30 minutes of treatment, 7 genes are altered. FIG. 1C. After 2 hours, 3 are altered. One transcript with unknown function, YGRO35C, is increased at both time points.

FIGS. 2A–2C. FIG. 2 depicts the changes in transcriptional effects of the wild type CDC28 versus mutant CDC28 F88G cells. FIG. 2A is a schematic drawing of CDC28 and the mutant CDC28. FIG. 2B. At 30 minutes, 22 gene transcripts were changed. FIG. 2C. At 120 minutes, 31 were changed. Eight of these genes are cell cycle regulated. Of these, 11 common gene transcripts were changed at both time points (7 increased: YDL241w, YHR071W, YMR095C, YMR096W, YNR065C, YOL058W, YPL1643; 4 decreased: YFL057C; YLL060C; YML116W; YOR313C).

FIG. 3 depicts transcriptional effects in the mutant CDC28 F88G cells on exposure for 30 minutes to the specific inhibitor of the mutant kinase, 4-amino-1-(tert-butyl)-3-(1'-naphthylmethyl)pyrazolo[3,4-d]pyrimidine. FIG. 3A is a schematic drawing of mutant CDC28 with and without the inhibitor. FIG. 3B. Eighty-five genes are altered: 74 decreased (of which 63 are cell cycle regulated); 11 increased (of which 5 are cell cycle regulated).

FIG. 4 depicts transcriptional effects in the mutant CDC28 F88G cells on exposure for 120 minutes to the specific inhibitor of the mutant kinase, 4-amino-1-(tert-butyl)-3-(1'-naphthylmethyl)pyrazolo[3,4-d]pyrimidine. FIG. 4A is a schematic drawing of mutant CDC28 with and without the inhibitor. FIG. 4B. One hundred and eighty-six genes are altered: 100 decreased (of which 82 are cell cycle regulated); 86 increased (of which 25 are cell cycle regulated). FIG. 4C. FIG. 4C is a continuation of FIG. 4B.

FIGS. 5A–G depict in tabular form the results of the experiment shown in FIGS. 1–4 wherein the particular genes whose levels increased or decreased changed more than 2-fold at 30 minutes or 120 minutes are described in more detail, with the fold-change in level indicated.

DETAILED DESCRIPTION OF THE INVENTION

Figure 1A:
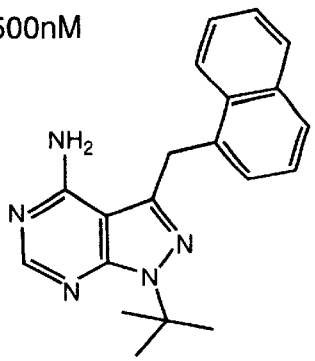
FIGS. 1A–1C.
Figure 1B:
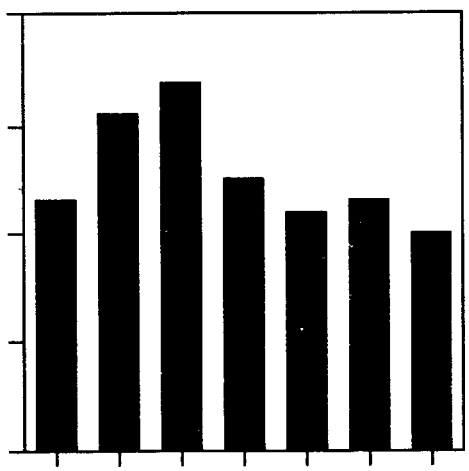
Figure 1C:
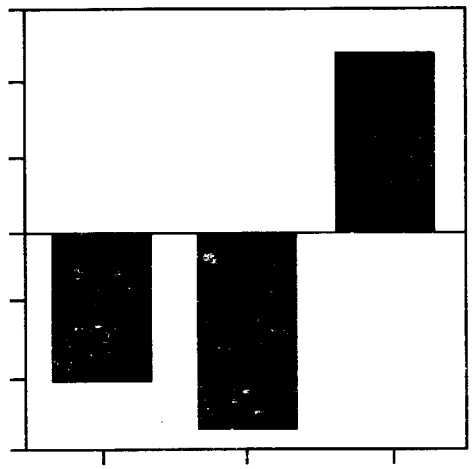

The inventors herein have made the surprising and remarkable discovery that a pattern of cellular responses attributable to the selective inhibition of a wild-type signaling molecule may be obtained by identifying the particular cellular responses of cells having a mutant form of the signaling molecule when exposed to a selective inhibitor of the mutant kinase, compared to responses of mutant cells not exposed to the inhibitor and optionally those of wild-type cells unexposed and exposed to the inhibitor. From the correlation among these conditions, a cellular response pattern attributable to the selective inhibition of the wild-type form of a particular signaling molecule may be obtained without the need for carrying out other more onerous procedures. As will be described in considerable detail below, the pattern of cellular responses, also referred to herein as a "fingerprint" or "blueprint," provides a facile means for identifying or screening selective inhibitors of the wild-type signaling molecule. This pattern may comprise a large number of data points, such as those obtained from DNA chip array technology. Some cellular responses may be altered upon exposure of the cell bearing the wild-type molecule to the selective inhibitor, and some may be unaltered. The present invention thus takes advantage of the difference in the overall response pattern attributable to the selective inhibition of the mutant molecule by the mutant inhibitor to provide a pattern with which to identify wild-type inhibitors. Selective inhibitors of the wild-type molecule are identified as those which produce a similar pattern of cellular responses as that of the mutant inhibitor on the mutant molecule. It is not necessary that the identities of the particular cellular responses are characterized or known, for example, the particular gene transcripts or expressed proteins, as the instant method relies upon the alterations in the patterns of such cellular responses and not their identities. Knowledge of these identities may provide additional confirmation as to the cellular role or function of the signaling molecule being inhibited.

While under no duty to disclose the theory under which the present invention operates, and not being bound by such a disclosure, the inventors herein, by preparing functionally silent mutants of signaling molecules, and furthermore preparing and evaluating selective inhibitors of these functionally silent mutants, found that the downstream cellular effects of the selective inhibition of the mutant signaling molecule, looked at comprehensively by changes in a plurality of cellular responses and with the proper controls, is mimicked by the downstream cellular effects of the selective inhibition of the wild-type molecule. Thus, using a mutant cell and a specific mutant inhibitor, a pattern may be identified which may then be applied to wild-type cells to identify specific inhibitors. Additional controls to optionally refine the method may be achieved by including the effects of the inhibitor on wild-type cells, as well as differences between the cellular responses between the wild-type and mutant cells, both in the absence of inhibitor.

As mentioned above, the pattern described herein is a correlation among several conditions and optional controls in which the outcome is the pattern of changes that are attributable to the selective inhibition of the particular signaling molecule of interest. The changes may be increases or decreases in particular cellular responses attributable to the inhibition of the particular molecule. Furthermore, the lack of a change in a particular cellular response may also be included among the pattern. A significant alteration that may be considered an effect contributing to the pattern is dependent upon the particular cellular response being measured, whether the measurement is qualitative or quantitative, and the reproducibility of measurement and other factors. Typically, in a specific, reproducible and quantitative measurement, a change of about 1.5 fold to about 2 fold increase or decrease (including appearance or disappearance) is considered a change resulting from the specific inhibition of the molecule. The identities of the particular elements of the cellular responses need not be determined, for example, the particular gene transcripts or proteins whose levels are altered. The skilled artisan will be aware of the variations in the measurement methods and the factors which must be considered in attributing the extent of change, or lack of a change, to a specific effect.

As noted above, the present invention has two broad aspects. In the first aspect, a method is provided to identify the pattern of cellular responses characteristic of or attributable to the selective inhibition of a wild-type signaling molecule, based upon data obtained using a mutant inhibitor and a mutant signaling molecule. In the second, the aforementioned pattern is utilized in identifying specific inhibitors.

The method of the present invention for identifying the pattern is carried out by any of the following general procedures. Various steps may be modified to achieve the same goal; such modifications will be readily apparent to the skilled artisan. To identify a pattern of cellular responses attributable to the selective inhibition of a wild-type form of a preselected signaling molecule the following steps may be carried out. The order in which the steps is carried out is important insofar as steps requiring the products of previous steps must await the preparation of the required products. Certain steps are optional, these steps providing additional comparisons to increase the discriminatory ability of the method. As will be noted below, such additional steps increase the time required for the test, but increase the power to identify selective inhibitors. Such additional steps may be excluded for high throughput screening, the steps added for increasing the discrimination.

First, a signaling molecule is selected, referred to herein as the preselected signaling molecule. A very large number of such molecules are known, and have been identified as being involved in a number of important cellular pathways. More details on the selection is provided below.

Next, cells are provided which express the wild-type form of the preselected signaling molecule. These cells are referred to herein as the wild-type cells. The origin or type of such cells will be those expressing the molecule, and may be from any organism, eukaryotic, or prokaryotic, including but not limited to mammalian such as human, other mammalian species, yeast, a plant, etc. The selection of the type of cell is not limiting, as it is dependent upon the molecule selected. The wild-type cells may be a cell of another species or even kingdom, engineered to express the wild-type form of a particular signaling molecule, to facilitate carrying out the method. Such engineered cells may be easier to grow and evaluate cellular responses than the natural cell in which the signaling molecule is expressed or is involved in cellular events. This step is optional for identifying the pattern attributable to inhibition, but such cells are used to screen candidate inhibitors.

In another step, mutant cells having a mutant preselected signaling molecule are provided. These cells have a mutant form of the preselected signaling molecule which either replaces or coexists with the wild-type form. The mutant signaling molecule is a functionally silent, mutant form of said preselected signaling molecule, such that the expression of a functional signaling molecule is not compromised in the cell under normal conditions. These mutant cells may have a pattern of cellular responses similar or identical to that of the wild-type cells; any differences in responses will be noted in correlating the various cellular responses among wild-type and mutant cells, as described below, in identifying the fingerprint of the signaling molecule useful for screening inhibitors.

Methods for preparing cells with a mutant form of a signaling molecule have been described and are known in the art. By way of non-limiting example, methods are described in copending application Serial No. PCT/US98/02522 (published as WO 98/35048). In this disclosure, the entire contents of which are incorporated herein by reference, mutants are engineered with particular specificity for inhibitors which are selective for the mutant signaling molecule and which do not inhibit the wild type signaling molecule. In the cited disclosure, methods for engineering of kinases and other mutli-substrate enzymes is described such that they can utilize modified substrates which are not as readily used by their wild-type forms. According to the invention, through enzyme engineering a structural distinction can be made between the nucleotide binding site of a protein kinase of interest, and the nucleotide binding sites of other kinases. This distinction allows the engineered kinase to use a nucleotide triphosphate or an inhibitor that is not as readily bound by the wild-type form of that kinase, or by other kinases. In a preferred embodiment with respect to the inhibitor, the inhibitor used is one that is "orthogonal" to the "natural" nucleotide triphosphate substrate for that kinase, or is orthogonal to a less specific inhibitor (e.g., one which is readily bound by the wild-type form of that kinase). Several criteria should be satisfied in engineering a kinase in order that it will be inhibited by the inhibitors of the present invention. The engineered mutant kinase should: (1) bind to an inhibitor which is bound less readily by wild-type protein kinases; preferably, the inhibitor will not substantially bind to wild-type kinases; and most preferably, will not bind at all to wild type kinases; (2) preferably, the engineered kinase will bind the inhibitor with high affinity (i.e., low $IC_{50}$). It is not generally of particular importance whether the inhibitor binds to the wild-type form of the kinase that corresponds to the engineered kinase, as such binding and the resulting inhibition would augment that of the engineered kinase. However, it is most likely that the wild-type form of that kinase will not bind the inhibitor any better than other wild-type kinases.

The mutant cell may be of any species of origin, expressing a mutant form of the signaling molecule derived from any species of origin. Thus, a plant signaling molecule may be provided in an animal cell, or an animal signaling molecule in a plant cell.

In a next step, an inhibitor of the mutant signaling protein is provided. The criteria of the mutant inhibitor are those as described above. The inhibitor, referred to herein as the mutant inhibitor, is a selective inhibitor of the mutant form of the preselected signaling molecule. Further examples of the methods of identifying mutant inhibitors are disclosed in copending application Serial No. 60/115,340, in which selective inhibitors of mutant protein kinases are disclosed, such as 4-amino-1-(tert-butyl)-3-(1'-naphthylmethyl) pyrazolo[3,4-d]pyrimidine, which is a selective inhibitor of the v-Src mutant v-Src I338G, and of the CDC28 mutant, CDC28 F88G. In brief, non-limiting methods of identifying selective inhibitor of said mutant cells includes using an altered form of a wild-type kinase inhibitor wherein an additional chemical functional group such as one that contains additional substituents is added to one or more sites on the wild-type inhibitor. Another method involves identifying a natural product or unnatural product that does not have to be derivatized to be a specific inhibitor of the mutant form of the signaling molecule, such as a molecule that was selected to exhibit mutant specific inhibition.

Once the foregoing wild-type cells, mutant cells, and the selective inhibitor of the mutant signaling molecule are obtained, the responses of the mutant cells, and optionally the wild-type cells, in the presence and absence of the mutant inhibitor are obtained. The types of cellular responses and method for measuring them are described in more detail below. In brief, the cellular responses may include any change or changes in any one or combination of cellular parameters which result from the inhibition of the signaling molecule, including but not limited to changes in gene transcription, protein expression, metabolic alterations, morphologic alterations, lipid alteration, and/or growth alteration. As noted above, the cellular responses provide a pattern or fingerprint of the cellular response to inhibition; such fingerprint may comprise a single type of change, such as in gene transcription products. As the characteristic pattern of cellular responses will usually comprise a plurality of different data points, for example, changes in transcription of a large number of gene products, or changes in expression of a large number of proteins, methods for identifying the cellular responses is preferably a method which can assess simultaneously the presence of a large number of data points. In this regard, DNA chip array technology, such as that described in U.S. Pat. No. 5,143, 854; WO92/10092; WO90/15070; U.S. Pat. Nos. 5,384,261; 5,545,531; 5,858,661; Yershov et al., (1996), Proc. Nat. Acad. Sci. U.S.A. 93:4913–4918; all of which are incorporated herein by reference, allows for the simultaneously measurement of a large number of unique mRNA transcripts. As noted above, the cellular responses may be of a single type, for example, mRNA or protein expression singly, or the fingerprint may comprise a combination of parameters, such as both mRNA and protein.

The identification of cellular responses is performed using the measurement method above, or a combination of measurement methods, on the following cells and under the following conditions:

(1) cellular responses exhibited by mutant cells unexposed to the mutant inhibitor; and (2) cellular responses exhibited by the mutant cells after exposure to the mutant inhibitor.

Optionally, either one or both of the following additional cellular responses may also be measured:

(3) cellular responses exhibited by the wild-type cells unexposed to the mutant inhibitor; or (4) cellular responses exhibited by the wild-type cells after exposure to the mutant inhibitor.

In the next step, the cellular responses of (1) and (2) above, optionally with (3) or (4) are compared to determine the cellular responses attributable to selective inhibition of the mutant molecule. For example, this determination of cellular responses attributable to selective inhibition may include the differences in mutant cells before and after exposure to the mutant inhibitor. The comparison may take into account cellular responses of wild-type cells not exposed to said mutant inhibitor which are unaltered in comparison to cellular responses of mutant cells unexposed to the mutant inhibitor, and cellular responses of said wild-type cells after exposure to the mutant inhibitor which are altered in comparison to the cellular responses in mutant cells exposed to the mutant inhibitor. Furthermore, the effects of the inhibitor on wild-type versus mutant cells may be taken into account. It will be apparent to the skilled artisan in comparing the various conditions described herein, some of which include combinations of selective effects and nonspecific effects, and controls which assist in identifying which effects are nonselective, that the overall pattern of cellular changes attributable to the selective inhibition is determined. The extent of a change is about 1.5 to about 2 fold increased or decreased over baseline. Appearance or disappearance of a cellular response is also considered an affected event. For example, using the CDC28 protein kinase and mutant CDC28 F88G as described in more detail in the examples below, and the selective inhibitor of this mutant, 4-amino-1-(tert-butyl)-3-(1'-naphthylmethyl)pyrazolo[3,4-d]pyrimidine, and wherein the pattern of cellular responses is gene transcription, measured using DNA chip array, among the 6000 or so genes in yeast whose transcription products may be identified by DNA chip array technology, the following results are obtained in the various tests described above: (1) 31 genes are altered in mutant cells unexposed to the mutant inhibitor, compared to wild-type cells; (2) 85 genes are altered in the mutant cells after a 30 minute exposure to the mutant inhibitor; of which 74 are decreases of more than two-fold, and 11 are increases more than two-fold; after a 120 minute exposure, 186 genes are altered, of which 100 are decreased and 86 are increased; (3) 22 genes are altered in wild-type cells unexposed to the mutant inhibitor; and (4) 7 genes are altered in the wild-type cells after exposure for 30 minutes to the mutant inhibitor; 3 genes are altered after a 120 minute exposure. By comparison of the above results on an altered gene-by-gene basis, a pattern of cellular changes is apparent. Non-specific changes comprise 1 common gene transcript changed from non-specific drug effects at both time points, and 11 common gene transcripts are changed from mutation effects at both time points. With regard to specific mutant inhibitor effects, at 30 minutes, 85 genes were altered, and at 120 minutes, 186 genes were altered. This pattern of alterations attributable to the specific inhibition of the mutant enzyme by the selective inhibitor thereof, taking into account the non-specific effects described above, provides a pattern which may be used to identify specific inhibitors of the wild-type protein kinase (see below). In the practice of the present invention for identifying selective inhibitors of the wild-type protein kinase, wild-type cells are exposed to candidate inhibitors of the wild-type kinase, and the gene expression measured as described above. Patterns matching or similar to that of the mutant inhibitor described above are those produced by specific inhibitors, thus allowing potential inhibitors to be identified. The extent of a match must be gauged somewhat subjectively, by comparing the extent of alterations by the candidate, wild-type inhibitor that match that of the mutant inhibitor on the mutant molecule; taking into consideration any additional genes that might be altered, in identifying a selective inhibitor. Of course, additional confirmatory tests on the identified inhibitors would be a normal course of experimentation by a skilled artisan once a compound is found that provides a match, such as the effect of the compound on the purified signaling molecule, as well as other measures of cellular changes induced by the candidate inhibitor, such as protein expression as well as gene transcription. Likely candidates, for example from the screening by the methods herein of vast libraries of compounds, would be advanced to more specific testing. Naturally, variations in the procedures above are within the realm usual experimental variations and are embraced herein. Additional considerations are provided below in the experimental design and interpretation.

In the Examples described herein, effects of the inhibitor were evaluated at 30 and 120 minutes. These two time points were chosen for this particular system based on the known time interval for yeast cell cycle progression which is about 90 minutes. Thus one time point shorter than the full cell cycle progression time (30 minutes) and one time point longer than the longest time point (120 minutes) were chosen. Naturally, the selection of the appropriate time point or points in the practice of the methods herein will depend on the type of cell being studied as well as the length of time the alterations in cellular responses occur after exposure to the particular inhibitor of the mutant molecule, and the candidate inhibitors being evaluated on the wild-type molecule. Further time considerations must be given is a stimulator is also used to initiate cellular events from which the patterns are discerned. The skilled artisan will be aware of these considerations and will be able to devise appropriate protocols based on the teachings herein.

Optionally, additional effects of particular compounds on wild-type and mutant cells may be performed, including but not limited to the effect of a non-specific inhibitor, such as but not limited to those described above, on cellular responses. The comparison among the above tests provides the fingerprint or pattern of cellular responses that allow for the identification of inhibitors of the wild-type signaling molecule. The basis of the comparison is as follows. As the mutant cells express a functionally silent mutation of the preselected signaling molecule compared to the wild type, the both the wild-type cells and the mutant cells without exposure to an inhibitor should produce a similar or identical series of cellular responses. These do not need to be identical, but the differences noted. Should the differences be significant, the mutant is probably not a functionally silent mutant as optimally required for the method, and will reduce the effectiveness of using the method of the present invention for the efficient screening of wild-type inhibitors.

A next, comparison is between the wild-type cells and the mutant cells exposed to the selective inhibitor of the mutant cells. As noted above, if the mutant signaling molecule is a functionally silent mutant and the mutant inhibitor is specific, the mutant inhibitor should affect cellular responses in the mutant cells to a much greater extent than that of the wild-type cells. The effect of the mutant inhibitor on the wild-type cells may include changes in cellular responses specific to the inhibition of the mutant molecule by the selective inhibitor, and those resulting from a generalized effect and not a specific effect on the signaling molecule or downstream cascade or effect. Thus, the controls utilizing a non-specific inhibitor, may be included to differentiate such non-specific effects from those differences in cellular responses of the mutant inhibitor on the mutant cells and the mutant inhibitor on the wild-type cells. By subtracting from the array of cellular responses of the mutant inhibitor on the mutant cells the expected fewer cellular responses of the mutant inhibitor on the wild-type cells, a pattern of cellular responses is obtained. Changes in these cellular responses are specific effects of the inhibition of the preselected signaling molecule. Thus, by performing the correlation among the four tests, optionally with the additional controls, a characteristic pattern of cellular responses consequent to the selective inhibition of the signaling molecule is obtained. As mentioned above, this pattern comprises cellular responses which are altered, as well as cellular responses which are unaltered.

It should be noted, as described above, that the controls described above and herein to identify the pattern of cellular responses attributable to selective inhibition of the mutant signaling molecule, and exclude nonselective inhibition, may be modified, or even eliminated, depending on the level of accuracy desired or acceptable for carrying out the test, for example, in screening large numbers of compounds. A less accurate but more rapid screen may be carried out by only determining the pattern of alterations resulting from the treatment of mutant cells with the selective inhibitor of the mutant molecule, and not winnowing from the large number of changes in that experiment those resulting from nonspecific inhibition or inhibition of the wild-type molecule by the mutant inhibitor. While the pattern will include a larger number of responses which are not selective, a rapid screening procedure and computerized analysis of the data, for example, using DNA chip array technology, could more rapidly identify potential candidates using this less accurate but higher throughput assay. Compounds identified as producing a pattern of responses in wild-type cells that is similar to that of the mutant system, by certain criteria, would then be candidates for more accurate screening in which all controls are used.

The extent of alteration representative of an effect on the particular cellular response is dependent upon the type of measurement. For example, as noted above, for mRNA levels, a change in either direction of about 1.5 fold to about 2 fold over the corresponding control is indicative of a cellular response attributable to the inhibitor. The extent of alteration of other measured of cellular response may be larger or smaller, depending on the variability of the methodology used for the measurement and the natural variability of the particular response.

The resultant pattern, which may also be called a fingerprint, of the above procedure allows for the subsequent screening of candidate inhibitors of the preselected signaling molecule. The screening method is performed by determining the changes in cellular responses induced by a candidate inhibitor on wild-type cells which express the preselected signaling molecule, to provide a pattern in the wild-type cells. Comparison of the pattern of cellular changes in the wild-type cells by the candidate inhibitor to the pattern obtained above allows for identifying selective inhibitors as those that are similar to or match the pattern. Thus, a selective inhibitor of the wild-type signaling molecule will, on exposure to cells having the wild-type molecule, produce a pattern of cellular responses that match the changes produced in mutant cells on exposure to the selective mutant inhibitor. As described in detail above, the pattern of cellular responses produced in mutant cells on exposure to the selective mutant inhibitor is attributable to or characteristic of the pattern of cellular responses produced in wild-type cells on exposure to a selective inhibitor of the wild-type signaling molecule. The procedure is to (a) identify a pattern of cellular responses attributable to the selective inhibition of a wild-type form of a preselected signaling molecule in accordance with the methods described above;

(b) expose wild-type cells to a candidate selective inhibitor of the wild-type form of the preselected signaling molecule;

(c) identifying the effect of the candidate inhibitor on the pattern of cellular responses in the wild-type cells; and (d) identifying a selective inhibitor as that with a pattern of cellular responses of the wild-type cells which resembles the pattern attributable to the inhibition of the wild-type form of the signaling molecule.

In carrying out the aforementioned procedure, the pattern of cellular responses of the wild-type cells to the candidate inhibitor is obtained in an analogous fashion to that described in detail above regarding obtaining the pattern in mutant cells having the mutant signaling molecule. Cellular responses in wild-type cells are determined before and after exposure to the candidate inhibitor. For high throughput screening, the unexposed wild-type cells is a single test to which each candidate compound's effect is compared to arrive at a pattern induced by or resulting from the effect of the candidate inhibitor on the wild-type cells. Additional controls optionally may be provided in a similar fashion to those in method for obtaining the pattern, but these may increase the time and effort required for high throughput screening, and thus may be avoided.

An extent of alteration of the components of the pattern of cellular expression may be about from 1.5 fold to about 2 fold, but this extent may change depending on the potency of the inhibitor. A dramatic extent in the level of alteration induced by a particularly potent inhibitor may be expected. As noted above, the comparison of matching is a combination of objective and subjective considerations, as the pattern of cellular responses attributable to inhibition of the mutant signaling molecule is matched by the inhibition of the wild-type molecule. The term attributable is used to refer to the cumulative and integrative information provided in the determination of the effects of the selective mutant inhibitor on the mutant cells to arrive at a pattern which if matched to a significant extent, represents the corresponding selective inhibition of the wild-type inhibitor of the wild-type cells.

Thus, comparison of the pattern obtained with the candidate inhibitor on wild-type cells to the pattern obtained as described above which is attributable to said inhibition, provides a method for identifying active inhibitors. A close or exact match indicates a high degree of specificity; a less perfect but similar match indicates activity. Based on the number of controls performed to obtain the pattern attributable to the inhibition of the wild-type signaling molecule, a match or similarity in the patterns may or may not provide evidence of the specificity of the inhibitor. As noted above, a less rigorous scree may be provided by reducing or eliminating certain optional controls in order to provide more rapid screening, with the need for more thorough analysis later of candidate compounds under more stringent conditions. The skilled artisan, based on the teaching herein, will design appropriate protocols to suit the particular screening objectives.

As noted above, the wild-type cell may be the natural host of the wild-type signaling molecule, or a cell engineered to harbor and express the signaling molecule gene, to simplify the screening of candidate inhibitors. A plant signaling molecule may be provided in an animal cell host, or an animal-derived signaling molecule may be provided in a plant cell host. Alternatively, prokaryotic cells may be the source or host of the molecule. Wild-type cell as referred to herein embraces the cell in which the wild-type signaling molecule resides for the conduct of the methods herein.

Furthermore, the above-mentioned method may utilize the pattern of cellular responses obtained with any one of the various comparisons, including the optional wild-type tests, in arriving at the results. If the pattern from the inhibition of the mutant signaling molecule by the mutant inhibitor was limited to the comparison of mutant cells unexposed and exposed to the mutant inhibitor, this pattern of cellular responses provided a more rapid but less discriminatory test.

The screening procedure may be performed in the presence of a stimulant to induce cellular responses. As in the procedure for identifying the pattern of cellular responses as well as in the screening procedure, the particular cellular responses of interest may or may not be constitutively exhibited by the cells being tested, and a stimulant may need to be provided to initiate a gene expression pattern or other programmed cell response which results in the cellular responses of interest, particularly as relate to the preselected signaling molecule of interest. For example, inhibitors are sought for a signaling molecule which participates in a cascade responsible for the downstream production of a toxic cytokine secreted from mesenchymal cells on exposure to a bacterial cell wall product. In order to obtain a fingerprint of the cellular responses of the cell to the inhibition of the signaling molecule, the cascade must be induced, which is performed by including the stimulant in the fingerprint identification procedure as well as the screening procedure. Other examples of such stimulants include hormones; cytokines; growth factors; heat; cold; light; metal ions; osmolarity changes; contact; homologous or heterologous cells; pressure; oxidative stress; natural products, such as from fermentation broths; plant extracts; marine organisms; synthetic compounds such as from pharmaceutical company libraries; combinatorial organic libraries; peptide libraries such as those displayed on bacteriophage, on solid beads such as polystyrene beads, tentagel beads; organ tissue explants; or via cell transfer into animals.

An additional control as mentioned above consists of exposing the cells to a non-specific inhibitor, such that may induce non-specific cellular responses which would not be exhibited by a selective inhibitor, and must be ignored in determining the pattern or fingerprint of the selective inhibitor. Examples of such non-specific inhibitors include 4-amino-1-tert-butyl-3-(p-methylphenyl)pyrazolo[3,4-d]pyrimidine (PP1), genestein, quercetin, K252a, UCN-01, staurosporine, adenosine, olomoucine, SKB 203580, damnacanthal, tyrphostins, erbstatin, piceatannol, lavendustin A, and radicicol. For example, staurosporine, K-252 and UCN-01 are known to be potent but nonspecific inhibitors of protein kinases [Ruegg U T, Burgess G M, Trends Pharmacol. Sci. (1989) 10:218–20]. Cellular responses induced by these compounds would not be expected to be a specific downstream effect of the inhibition of the preselected signaling molecule. They may be inhibitors of a broader class or subclass of signaling molecules than the wild-type and mutant molecules being studied.

As mentioned above, a large number of signaling molecules are candidates for the preselected signaling molecule in the present invention. Non-limiting examples of groups of such molecules include transcription factors, ATP-dependent phosphotransferases, myosin motors, histone acetyl transferases, ion channels, famesyl transferases, ligand gated channels, metabolic enzymes, natural product targets, the proteosome, ubiquitin pathway enzymes, complement system enzymes, proteases, intracellular stores of ions, vesicle trafficking enzymes, G-protein coupled receptors, proteases, and signal transduction molecules. Examples of eukaryotic transcription factors include transcription factor IID (TFIID) and TFIIA. Examples of ATP-dependent phosphotransferases include protein kinases, lipid kinases, inositol kinases, non-classical protein kinases. Examples of myosin motors include myosin 1 beta, and myosin 5.

Examples of specific protein kinases capable of being used in the methods herein comprise those set forth in the following classification scheme:
1. AGC Group (protein kinases A, G and C)
    1. AGC Group I
        Cyclic nucleotide regulated protein kinase (PKA & PKG) family
    2. AGC Group II
        Diacylglycerol-activated/phospholipid-dependent protein kinase C (PKC) family
    3. AGC Group III
        Related to PKA and PKC (RAC/Akt) protein kinase family
    4. AGC Group IV
        Kinases that phoshorylate G protein-coupled receptors family
    5. AGC Group V
        Budding yeast AGC-related protein kinase family
    6. AGC group VI
        Kinases that phosphorylate ribosomal protein S6 family
    7. AGC Group VII
        Budding yeast DBF2/20 family
    8. AGC Group VIII
        Flowering plant PVPK1 protein kinase homolog family
    9. AGC Group Other
        Other AGC related kinase families
2. Calmodulin Dependent Protein Kinase (CaMK) Group
    1. CaMK Group I
        Kinases regulated by Ca2+/CaM and close relatives family
    2. CaMK Group II
        KIN1/SNF1/Nim1 family
    3. CaMK Other
        Other CaMK related kinase families
3. CMGC Group
    1. CMGC Group I
        Cyclin-dependent kinases (CDKs) and close relatives family
    2. CMGC Group II
        ERK (MAP) kinase family
    3. CMGC Group III
        Glycogen synthase kinase 3 (GSK3) family
    4. CMGC Group IV
        Casein kinase II family
    5. CMGC Group V
        Clk family
    6. CMGC Group Other
4. Protein Tyrosine Kinase (PTK) Group—'Conventional' protein-tyrosine kinases Group I–IX Non-membrane spanning protein-tyrosine kinases Group IX–XXI membrane spanning protein-tyrosine kinases
    1. PTK group I
        Src family
    2. PTK Group II
        Tec/Atk family
    3. PTK Group III
        Csk family
    4. PTK Group IV
        Fes (Fps) family
    5. PTK Group V
        Abl family
    6. PTK Group VI
        Syk/ZAP70 family
    7. PTK Group VII
        Tyk2/Jak1 family
    8. PTK Group VIII
        Ack family
    9. PTK Group IX
        Focal adhesion kinase (Fak) family
    10. PTK Group X
        Epidermal growth factor receptor family
    11. PTK Group XI
        Eph/Elk/Eck receptor family
    12. PTK Group XII
        Axl family
    13. PTK Group XIII
        Tie/Tek family
    14. PTK Group XIV
        Platelet-derived growth factor receptor family
    15. PTK Group XV
        Fibroblast growth factor receptor family
    16. PTK Group XVI
        Insulin receptor family
    17. PTK Group XVII
        LTK/ALK family
    18. PTK Group XVIII
        Ros/Sevenless family
    19. PTK Group XIX
        Trk/Ror family
    20. PTK Group XX
        DDR/TKT family
    21. PTK Group XXI
        Hepatocyte growth factor receptor family
    22. PTK Group XXII
        Nematode Kin 15/16 family
    23. PTK Other membrane spanning kinases
        Other PTK kinase families
5. Other Protein Kinase (OPK) Group—Other protein kinases (not falling in major groups)
    1. OPK Group I
        Polo family
    2. OPK Group II
        MEK/STE7 family
    3. OPK Group III
        PAK/STE20 family
    4. OPK Group IV
        MEKK/STE11 family
    5. OPK Group V
        NimA family
    6. OPK Group VI
        wee1/mik1 family
    7. OPK Group VII
        Kinases involved in transcriptional control family 8. OPK Group VIII
   Raf family
9. OPK Group IX
   Activin/TGFb receptor family
10. OPK Group X
    Flowering plant putative receptor kinases and close relatives family
11. OPK Group XI
    PSK/PTK "mixed lineage" leucine zipper domain family
12. OPK Group XII
    Casein kinase I family
13. OPK Group XIII
    PKN prokaryotic protein kinase family
14. OPK Other
    Other protein kinase families (each with no close relatives)

As mentioned above, cellular responses include but are not limited to gene transcription, protein expression, metabolic alteration, morphologic alteration, lipid alteration, growth alteration, cell shape change, cytoskeletal reorganization, protein translocation, protein relocalization, metal ion influx, metal ion efflux, change in osmolarity, receptor expression on the cell surface, receptor clustering, receptor desensitization, protein glycosylation, protein destruction, protein phosphorylation or other protein post-translational modification. Furthermore, and as noted herein, the specific cellular responses need not be characterized as the methods described herein are based upon alterations in patterns and not in the identities of the individual cellular responses making up the pattern. For example, the alterations in the levels of various expressed proteins as determined by 2-dimensional gel electrophoresis may be compared among cells untreated and treated in accordance with the present invention. The proteins in which alterations in expression levels are attributable to selective inhibition of the mutant signaling protein comprise the pattern, even in the absence of knowledge as to the identities of the particular altered proteins comprising the pattern. Naturally, knowledge of the proteins may assist in further characterizing the particular signaling molecule and its downstream targets, but this knowledge is not necessary to identify the pattern which is then useful for identifying selective inhibitors of the wild type molecule.

Various methods are available for measuring each of these cellular responses. For example, gene transcription may be measured by DNA chip array technology, cDNA array techniques on glass or nitrocellulose filters, oligonucleotide arrays on various solid supports, TAQman assay, quantitative PCR, competitive PCR, and differential display, also genetic methods including random or non-random insertion of promotorless reporter genes such as green fluorescence protein, luciferase, betalactamase, fluorescence activated cell sorter analysis, fluorescence microscope analysis, and antibody staining for extracellular ligands or intracellular ligands. Such methods are known to one of ordinary skill in the art. In a preferred embodiment, DNA chip array technology is used to measure cellular responses.

If protein expression is a measure of cellular responses, protein may be measured by methods such as differential display, 2-D protein gel electrophoresis, mass spectroscopy, high-throughput mass spectroscopy, massively parallel protein identification technologies such as those based on monoclonal or polyclonal antibody recognition, RNA or DNA polymers which recognize various proteins, such RNA or DNA molecules could be produced from so-called in vitro evolution experiments, high-throughput confocal microscopy, X-ray diffraction, nuclear magnetic resonance spectroscopy, resonance raman spectroscopy, and capillary electrophoresis methods. Such methods are known to one of ordinary skill in the art.

Non-limiting examples of methods for the preparation of mutants of signaling molecules and identification of selective inhibitors of mutant signaling molecules are described in copending applications Serial Nos. 60/115,340 and PCT/US98/02522 (published as WO 98/35048), incorporated herein by reference. These citations provide examples of these steps of the present invention; other, alternative methods are embraced herein.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Identification of a Specific Pattern of Cellular Changes

Yeast cells expressing a functionally silent, mutant form of the wild-type protein kinase CDC28, termed CDC28 F88G, were prepared by the methods of standard yeast genetics as described in "Guide to Yeast Genetics and Molecular Biology" (Methods in Enzymology, Vol.194) by Christine Guthrie, Gerald R. Fink (Editor) Vol 194 (February 1991) Academic Press. A selective inhibitor of the mutant kinase, with little effect on the wild-type kinase, was prepared and identified using the methods described in Application Serial No. 60/115,340. Using DNA chip array technology, the levels of 6100 gene transcripts were quantitated in mRNA isolated from yeast cells expressing either wild type or F88G (mutant) CDC28 protein kinase either untreated or treated for 30 minutes or 120 minutes with 500 nanomolar (nM) 4-amino-1-(tert-butyl)-3-(1'-naphthylmethyl)pyrazolo[3,4-d]pyrimidine dissolved in DMSO (500) or simply DMSO (DMSO). A change is defined as 2 fold increase or decrease in a gene transcript that is present or absent only in a particular sample. Methods for measuring transcripts were those described in Wodicka L, Dong H, Mittmann M, Ho M H, Lockhart D J, Genome-wide expression monitoring in Saccharomyces cerevisiae, Nat. Biotechnol. (1997) 15:1359–67. The results and comparisons among the gene transcripts are shown in FIGS. 1–4, with the identities of the particular gene transcripts listed in FIG. 5. Non-specific drug effects are the result of the exposure of the inhibitor to wild-type cells. The mutation effects are indicated by the alterations between the expression pattern between the mutant cells and the wild-type cells, both in the absence of inhibitor. The results of specific inhibition are shown by the differences between the mutant cells before and after exposure to the inhibitor, including increases and decreases. Effects of the inhibitor were evaluated at 30 and 120 minutes. These two time points were chosen based on the known time interval for yeast cell cycle progression which is about 90 minutes. Thus one time point shorter than the full cell cycle progression time (30 minutes) and one time point longer than the longest time point (120 minutes) were chosen. The comparisons of results are shown in FIGS. 1–4, and the details of the particular transcripts altered in FIG. 5.

Figure 2A:
Figure 2B:
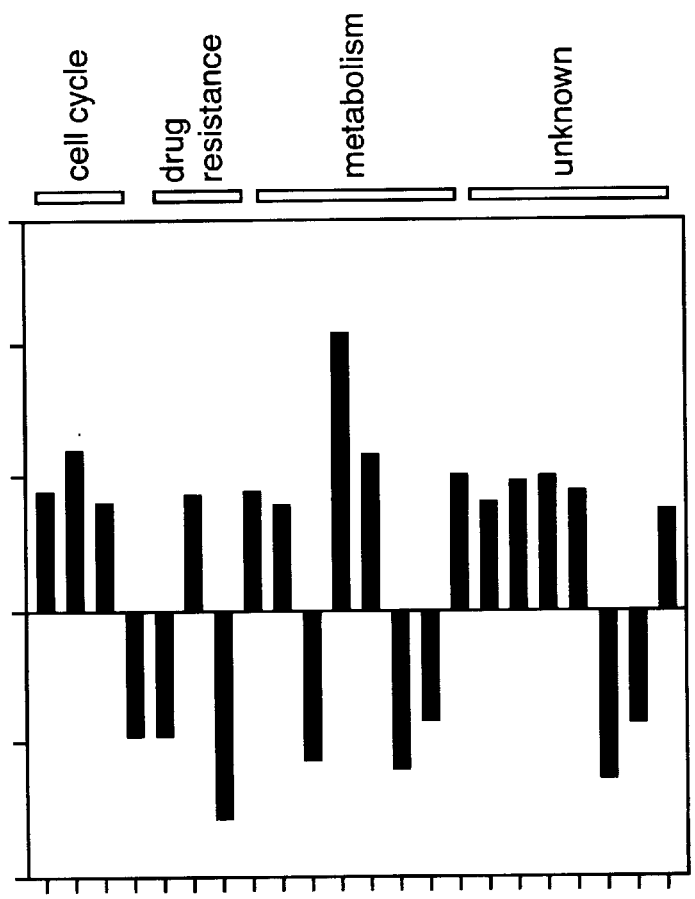
Figure 3A:
FIGS. 3A–B.
Figure 3B:
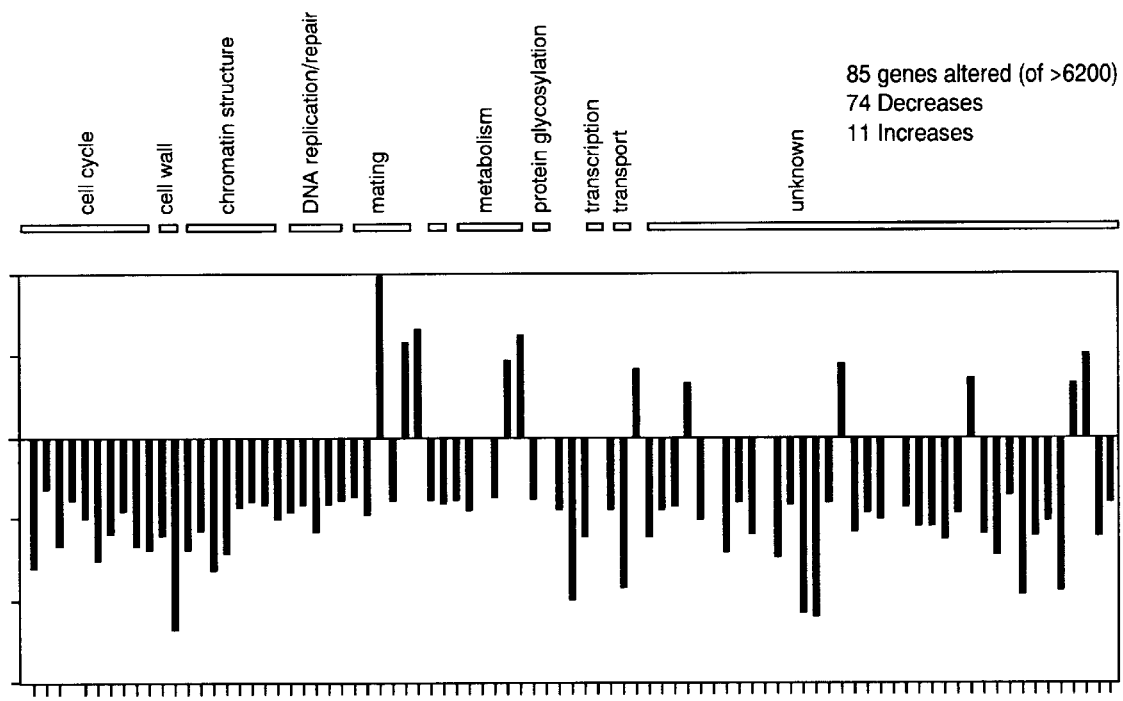
Figure 4A:
FIGS. 4A–C.
Figure 4B:
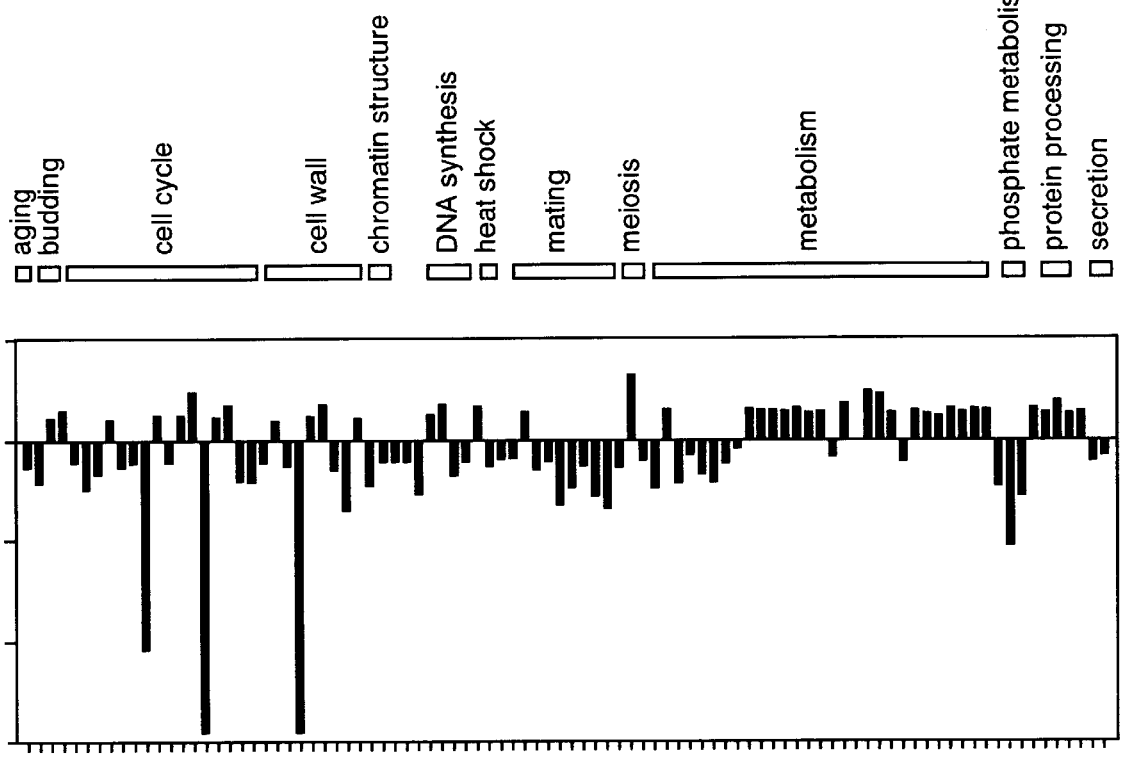
Figure 4C:
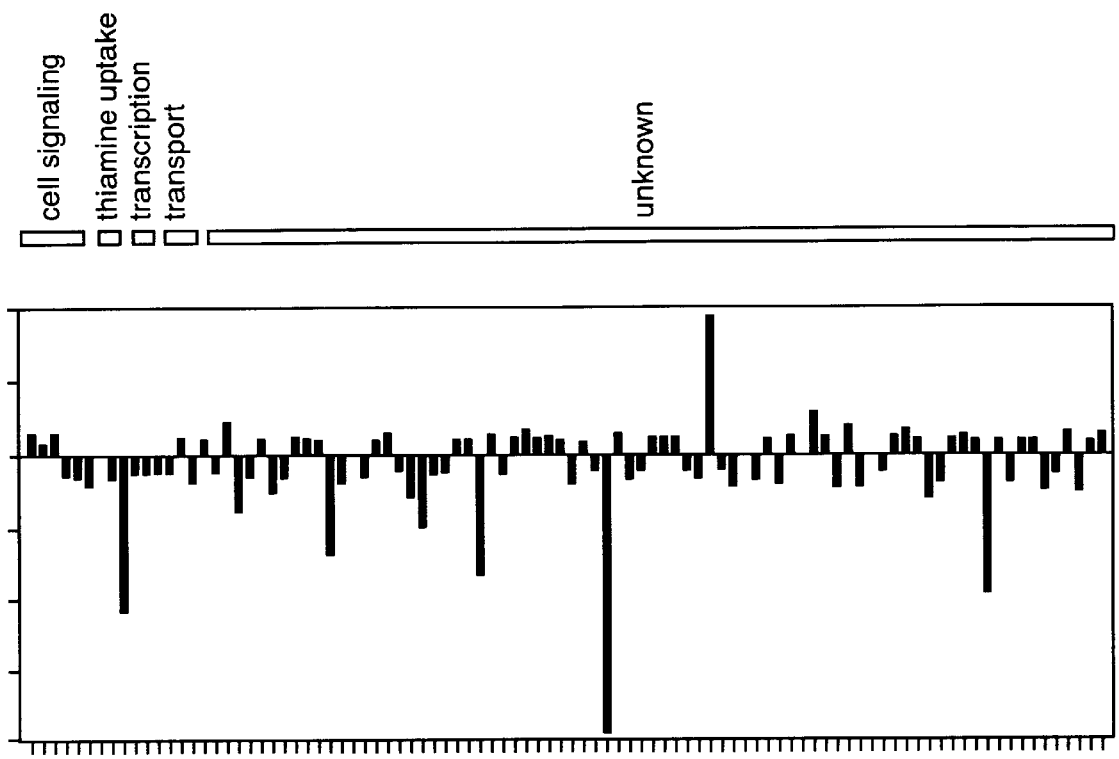

Among all 6100 yeast genes whose transcripts were determined, roughly 800 (13%) are cell cycle regulated. The non-specific results showed that 1 gene transcript changed from non-specific drug effects in both time points (FIG. 1), and 11 gene transcripts changed from mutation effects in both time points (FIG. 2).

After the 30 minute incubation (FIG. 3), the following results were obtained: 7 gene transcripts changed from non-specific drug effects (1/7 is cell cycle regulated); 22 gene transcripts changed from mutation effects (8/22 are cell cycle regulated); 74 gene transcripts decreased from specific inhibition of mutant CDC28 (63/74 are cell cycle regulated; and 11 gene transcripts increased from specific inhibition of mutant CDC28 (5/11 are cell cycle regulated). Based on these data, it is apparent that gene transcripts that decrease from specific inhibition of mutant CDC28 are largely ones that have peak expression at the G2/M checkpoint of the cell cycle. Gene transcripts that increase from specific inhibition of mutant CDC28 are largely ones that are involved in yeast mating.

After 120 minute exposure to the inhibitor (FIG. 4), 3 gene transcripts changed from non-specific drug effects (1/3 is cell cycle regulated); 31 gene transcripts changed from mutation effects (8/31 are cell cycle regulated); 100 gene transcripts decreased from specific inhibition of mutant CDC28 (82/100 are cell cycle regulated); and 86 gene transcripts increased from specific inhibition of mutant CDC28 (25/86 are cell cycle regulated). Gene transcripts that decrease from specific inhibition of mutant CDC28 are largely ones that have peak expression at the G2/M checkpoint of the cell cycle (same as 30 minute). Gene transcripts that increase from specific inhibition of mutant CDC28 are largely ones that have peak expression during G1 of the cell cycle.

The genes identified as specifically decreased or increased in response to specific inhibition of CDC28 F88G are understood as being "downstream" of CDC28 or effectors of CDC28 function. As such, if other strategies are used to target these genes such as traditional drug development strategies, the effect on the cell or organism may be expected to be similar to the effect of inhibiting CDC28.

EXAMPLE 2

Identification of Selective Inhibitors of Wild-type Signaling Molecules

A selective inhibitor of the wild-type CDC28 protein kinase is identified as follows. Wild-type yeast expressing the CDC28 gene are exposed to candidate inhibitors for 30 minutes and 120 minutes, and the gene expression pattern of the cells is measured using DNA chip array technology in the same fashion as described in Example 1. Gene transcripts which change more than a factor of two (increased or decreased) compared to the level expressed in untreated wild-type cells are identified. This pattern of altered gene transcript level is compared to that obtained in Example 1 for the selective inhibition of the mutant form of the protein kinase, at the time points indicated. A compound that produces a pattern of changes that matches, is highly similar to, or resembles, that of the mutant kinase obtained in Example 1 is a selective inhibitor of the wild-type kinase.

EXAMPLE 3

Identification of Specific Inhibitors in Human Cells

A pattern of cellular responses in human cells expressing the wild-type form and a mutant form of v-Src (v-Src and v-Src I338G, respectively) was identified using expressed proteins, measured by 2-D gels, in accordance with the procedures described in Example 1 above. The specific inhibitor of the mutant enzyme was 4-amino-1-(tert-butyl)-3-(1'-naphthyl)pyrazolo[3,4-d]pyrimidine. After comparison of the data from the particular experiments, a group of expressed proteins were identified of which alterations in their levels is attributed to specific inhibition of the mutant kinase.

Using the pattern obtained above, a library of compounds is screened using wild-type cells expressing v-Src for alterations in the same proteins identified above as being attributable to selective inhibition. Compounds with identical or similar patterns to those above are identified as selective inhibitors of the wild-type kinase.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

LITERATURE CITATIONS

1. Mustelin, T. 1994. T Cell antigen receptor signaling: Three families of tyrosine kinases and a phosphatase. *Immunity.* 1: p. 351–356.
2. Renshaw, M. W., E. T. Kipreos, M. R. Albrecht, and J. Y. J. Wang 1992. Oncogenic v-Abl tyrosine kinase can inhibit or stimulate growth, depending on the cell context. *EMBO J* 11(11): p. 3941–3951.
3. Cohen, G. B., R. Rein, and D. Baltimore 1995. Modular Binding Domains in Signal Transduction Proteins. *Cell.* 80: p. 237–248.
4. Hunter, T. 1987. A Thousand and One Protein Kinases. *Cell.* 50: p. 823–829.
5. Eiseman, E. and J. B. Bolen 1992. Engagement of the high-affinity IgE receptor activates src protein-related tyrosine kinases. *Nature.* 355.
6. Murray, A. W. 1994. Cyclin-dependent kinases: regulators of the cell cycle and more. *Chem. and Bio.* 1(4): p. 191–195.
7. White, M. F. 1991. Mini-Review: Structure and Function of Tyrosine Kinase Receptors. *J. Bioenergetics Biomem.* 23(1): p. 63–83.
8. Hunter, T. 1995. Protein Kinases and Phosphatases: The Yin and Yang of Protein Phosphorylation and Signaling. *Cell.* 80: p. 225–236.
9. Sawyers, C. L. 1992. The bcr-abl gene in chronic myelogenous leudaemia. *Cancer Surveys.* 15: p. 37–51.
10. Crabtree, G. R. and N. A. Clipstone 1994. Signal Transmission between the plasma membrane and nucleus of T lymphocytes. *Annu. Rev. Biochem.* 63: p. 1045–1083.
11. Kurzrock, R., J. U. Gutterman, and M. Talpaz 1988. The molecular genetics of Philadelphia chromosome-positive leukemias. *New Engl. J. Med.* 319(15): p. 990–998.
12. Ullrich, A. and J. Schlessinger 1990. Signal transduction by receptors with tyrosine kinase activity. *Cell.* 61: p. 203–212.
13. Bolen, J. B., R. B. Rowley, C. Spana, and A. Y. Tsygankov 1992. The Src family of tyrosine protein kinases in hemopoietic signal transduction. *FASEB.* 6: p. 3403–3409.

14. Cicchetti, P., B. J. Mayer, G. Thiel, and D. Baltimore 1992. Identification of a Protein that binds to the SH3 region of Abl and is similar to Bcr and GAP-rho. *Science.* 257: p. 803–806.
15. Sawyers, C. L., J. McLaughlin, A. Goga, M. Havlik, and O. Witte 1994. The nuclear tyrosine kinase c-Abl negatively regulates cell growth. *Cell.* 77: p. 121–131.
16. Kipreos, E. T. and J. Y. J. Wang 1992. Cell Cycle-regulated binding of c-abl Tyrosine kinase to DNA. *Science.* 256: p. 382–385.
17. Velazquez, L., M. Fellous, G. R. Stark, and S. Pellegrini 1992. *Cell.* 70: p. 313–320.
21. Muller, A. J., A. -M. Pendergast, K. Parmar, M. H. Havlik, N. Rosenberg, and O. N. Witte 1993. En Bloc substitution of the Src homology region 2 domain activates the transforming potential of the c-abl protein tyrosine kinase. *Proc. Natl. Acad. Sci., USA.* 90: p. 3457–3461.
22. Mayer, B. J. and D. Baltimore 1994. Mutagenic analysis of the roles of SH2 and SH3 domains in regulation of the abl tyrosine kinase. *Mol Cell. Bio.* 14(5): p. 2883.
23. Mayer, B. J., P. K. Jackson, R. A. Van Etten, and D. Baltimore 1992. Point Mutations in the abl SH2 domain coordinately impair phosphotyrosine binding in vitro and transforming activity in vivo. *Mol. Cell. Bio.* 12(2): p. 609–618.
24. Koyama, S., H. Yu, D. C. Dalgarno, T. B. Shin, L. D. Zydowsky, and S. L. Schreiber 1993. Structure of the P13K SH3 domain and analysis of the SH3 Family. *Cell.* 72: p. 945–952.
25. Yu, H., M. K. Rosen, T. B. Shin, C. Seidel-Dugan, J. S. Brugge, and S. L. Schreiber 1992. Solution Structure of the SH3 domain of Src and identification of its ligand-binding site. *Science.* 258: p. 1665–1668.
26. Kohda, D., H. Hatanaka, M. Odaka, V. Mandiyan, A. Ullrich, J. Schlessinger, and F. Inagaki 1993. Solution Structure of the SH3 domain of phospholipase C-gamma *Cell.* 72: p. 953–960.
27. Waksman, G., S. E. Shoelson, N. Pant, D. Cowburn, and J. Kuriyan 1993. Crystal structure/NMR of SH2. *Cell.* 72: p. 779–790.
28. Eck, M. J., S. E. Shoelson, and S. C. Harrison 1993. SH2 crystal structure. *Nature.* 362: p. 87.
32. Brugge, J. S. & Erikson, R. L. 1977. *Nature* 269(5626), 346–8.
33. Jove, R. & Hanafusa, H. 1987. *Ann. Rev. Cell Biol.* 3, 31–56.
34. Erpel, T. & Courtneidge, S. A. 1995. *Curr. Op. in Cell Biology* 7, 176–182.
35. Pawson, T. 1995. *Nature* 373, 573–580.
36. Waksman, G., Kominos, D., Robertson, S. C., Pant, N., Baltimore, D., Birge, R. B., Cowburn, D., Hanafusa, H., Mayer, B. J., Overduin, M., Resh, M. D., Rios, C. B., Silverman, L. & Kuriyan, J. 1992). *Nature* 358, 646–653.
37. Taylor, S. J. & Shalloway, D. 1993. *Curr. Opin. Genet. Dev.* 3, 26–34.
38. Brown, M. T. & Cooper, J. A. 1996. *Biochemica et Biophysica Acta* 1287, 121–149.
39. Songyang, Z., Carraway, K. L. I., Eck, M. J., Harrison, S. C., Feldman, R. A., Mohammadi, M., Schlessinger, J., Hubbard, S. R., Smith, D. P., Eng, C., Lorenzo, M. J., Ponder, B. A. J., Mayer, B. J. & Cantley, L. C. 1995. *Nature* 373, 536–539.
40. Kamps, M. P. & Sefton, B. M. 1988. *Oncogene Res.* 3, 105–115.
72. *Principles of Biochemistry*, A. Lehninger, D. Nelson and M. Cox, 2nd Ed., 1993. Worth Publishers, New York, ISBN 0-87901-500-4.
73. C. R. Faltynek, et al. 1995. *Biochemistry* 34, 12404–10.
74. J. Hanke, et al. 1996. *J. Biol. Chem.* 271, 695–701.

What is claimed is:

1. A method for identifying a pattern of one or more cellular responses attributable to selective inhibition of a wild-type signaling molecule comprising:
   (a) providing mutant cells expressing a mutant form of the wild-type signaling molecule, wherein the mutant form of the wild-type signaling molecule retains the function of the wild-type signaling molecule;
   (b) contacting said mutant cells with an inhibitor, said inhibitor being a selective inhibitor of said mutant form of the wild-type signaling molecule;
   (c) identifying one or more cellular responses exhibited by said mutant cells before and after contact with said inhibitor;
   (d) comparing said one or more cellular responses obtained in step (c) to identify a pattern of cellular responses exhibited by said mutant cells after said contact; and,
   (e) comparing the pattern obtained in step (d) to a pattern of one or more cellular responses obtained from the wild-type signaling molecule, wherein, when said wild-type signaling molecule pattern comprises one or more cellular responses which are characteristic of one or more cellular responses of the pattern of the inhibition of said mutant form of the wild-type signaling molecule, a pattern of one or more cellular responses attributable to selective inhibition of a wild-type signaling molecule is identified.

2. The method of claim 1 further comprising wild-type cells comprising the wild-type signaling molecule and identifying a second set of one or more cellular responses selected from the group consisting of:
   (i) wild-type cells not contacted with said inhibitor, said wild-type cells having said wild-type signaling molecule;
   (ii) wild-type cells contacted with said inhibitor; and,
   (iii) the combination thereof.

3. The method of claim 1 further comprising wild-type cells comprising the wild-type signaling molecule wherein said wild-type cells and/or said mutant cells are contacted with a stimulant in step (b) to induce said one or more cellular responses.

4. The method of claim 3 wherein said stimulant is selected from the group consisting of hormones, cytokines, growth factors, heat, cold, light, metal ions, osmolarity changes, contact, homologous cells, heterologous cells, pressure, oxidative stress, natural products, plant extracts, marine organisms, synthetic compounds, combinatorial organic libraries, peptide libraries, organ tissue explants, and via cell transfer into animals.

5. The method of claim 1 wherein said wild-type signaling molecule is selected from the group consisting of ATP-dependent phosphotransferases, myosin motors, histone acetyl transferases, ion channels, farnesyl transferases, metabolic enzymes, ubiquitin pathway enzymes, complement system enzymes, proteases, and vesicle trafficking enzymes.

6. The method of claim 5 wherein said wild-type signaling molecule is an ATP-dependent phosphotransferase selected from the group consisting of protein kinases, lipid kinases, inositol kinases, non-classical protein kinases, histidine kinases, aspartyl kinases, nucleoside kinases, and polynucleotide kinases.

7. The method of claim 6 wherein said ATP-dependent phosphotransferase is a protein kinase selected from the group consisting of AGCs, calmodulin dependent protein kinases, CMGCs, protein tyrosine kinases, and other protein kinases.

8. The method of claim 6 wherein said ATP-dependent phosphotransferase is a protein kinase and is CDC28 from the yeast *S. cerevesiae* or human CDK2.

9. The method of claim 1 wherein said one or more cellular responses are selected from the group consisting of gene transcription, protein expression, metabolic alteration, morphologic alteration, lipid alteration, growth alteration, cell shape change, cytoskeletal reorganization, protein translocation, protein relocalization, metal ion influx, metal ion efflux, change in osmolarity, receptor expression on the cell surface, receptor clustering, receptor desensitization, protein glycosylation, protein destruction, protein phosphorylation and other protein post-translational modification.

10. The method of claim 9 wherein said one or more cellular responses is gene transcription measured by a method selected from the group consisting of DNA chip array technology, cDNA array techniques on glass or nitrocellulose filters, oligonucleotide arrays on various solid supports, TAQman assay, quantitative PCR, competitive PCR, and differential display.

11. The method of claim 9 wherein said cellular response is protein expression measured by a method selected from the group consisting of differential display, 2-D protein gel electrophoresis, mass spectroscopy, and high-throughput mass spectroscopy.

12. The method of claim 1 wherein said cells are animal, plant, protist, or prokaryotic cells.

13. The method of claim 1 wherein said mutant form of the signaling molecule replaces the wild-type signaling molecule in said mutant cells.

14. The method of claim 1 wherein said mutant cells are prepared by a method selected from the group consisting of
    (a) gene knock-in technology;
    (b) mating or fusion between an organism or cell lacking a gene encoding the wild type signaling molecule and an organism or cell which contains one or more genes encoding both the wild type signaling molecule and the mutant form of the wild-type signaling molecule to produce progeny, screening said progeny; and, selecting progeny comprising the gene encoding the mutant form of the signaling molecule and lacking the gene encoding the wild-type signaling molecule.

15. The method of claim 1 wherein said mutant cells express both the mutant form of the wild-type signaling molecule and the wild-type signaling molecule.

16. The method of claim 15 wherein said mutant cells are prepared by transfection of wild-type cells with a plasmid DNA encoding the mutant signaling molecule, or in the case of prokaryotic cells, transformation of said wild-type cells with a plasmid DNA encoding the mutant signaling molecule.

17. The method of claim 1 wherein said inhibitor is an altered form of a wild-type signaling molecule inhibitor wherein an additional chemical functional group is added to one or more sites on the wild-type signaling molecule inhibitor.

18. The method of claim 1 wherein said wild-type signaling molecule and the said mutant form of the wild-type signaling molecule, respectively, are selected from the group consisting of CDC28 and CDC28 F88G, v-Src and v-Src I338G, c-AMP dependent kinase (PKA) and PKA M120G, c-AMP dependent kinase (PKA) and PKA M120A, p38 and p38 T106A, p38 and p38 T106G, Raf and Raf (V420A), Raf and Raf (V420G), and the insulin receptor kinase (IRK) IRK (V1075A) and IRK (V1075G).

19. The method of claim 1 wherein said wild-type signaling molecule and said mutant form of the wild-type signaling molecule are CDC28 and CDC28 F88G, said inhibitor is 4-amino-1-(tert-butyl)-3-(1'-naphthylmethyl) pyrazolo[3,4-d]pyrimidine, and said cellular responses are gene transcription products.

20. The method of claim 19 wherein said gene transcription products are measured by DNA chip array technology.

21. The method of claim 7 additionally comprising the step of contacting said mutant cells with a non-specific inhibitor, wherein said pattern of one or more cellular responses additionally comprises cellular responses which are altered or unaltered by said non-specific inhibitor.

22. The method of claim 21 wherein said non-specific inhibitor is selected from the group consisting of PP I, genestein, quercetin, K252a, staurosporine, adenosine, olomoucine, SKB 203580, damnacanthal, tyrphostins, erbstatin, piceatannol, lavendustin A, and radicicol.

23. A pattern of one or more cellular responses generated by the method of claim 1.

24. A method for identifying a pattern of one or more cellular responses attributable to the selective inhibition of a wild-type signaling molecule comprising:
    (a) providing mutant cells expressing a mutant form of the wild-type signaling molecule, said mutant cells comprising a substitution of a mutant form of said wild-type signaling molecule for the corresponding wild-type signaling molecule, wherein said mutant form of the wild-type signaling molecule retains the same function as the wild-type signaling molecule;
    (b) contacting said mutant cells with an inhibitor, said inhibitor being a selective inhibitor of said mutant form of the wild-type signaling molecule;
    (c) identifying one or more cellular responses exhibited by said mutant cells before and after contact with said inhibitor,
    (d) comparing said one or more cellular responses obtained in step (c) to identify a pattern of one or more cellular responses exhibited by said mutant cells after said contact; and,
    (e) comparing the pattern obtained in step (d) to a pattern of one or more cellular responses obtained from the wild-type signaling molecule, wherein, when said wild-type signaling molecule pattern comprises one or more cellular responses which are characteristic of one or more cellular responses of the pattern of the inhibition of said mutant form of the wild-type signaling molecule, a pattern of one or more cellular responses attributable to selective inhibition of a wild-type signaling molecule is identified.

25. The method of claim 24 further comprising identifying a second set of one or more cellular responses selected from the group consisting of:
    (i) wild-type cells not contacted with said inhibitor, said wild-type cells having said wild-type signaling molecule,
    (ii) wild-type cells after contact with said inhibitor, and
    (iii) the combination thereof.

26. A method for identifying a pattern of one or more cellular responses attributable to the selective inhibition of a wild-type signaling molecule comprising:
    (a) providing wild-type cells having a wild-type signaling molecule;
    (b) providing mutant cells having a mutant form of the wild-type signaling molecule, said mutant form of the wild-type signaling molecule having the same function as the wild-type signaling molecule;

(c) contacting the mutant cells with an inhibitor selective for the mutant form of the wild-type signaling molecule;

(d) identifying one or more cellular responses exhibited by said wild-type cells not contacted with said inhibitor;

(e) identifying one or more cellular responses exhibited by said wild-type cells contacted with said inhibitor;

(f) identifying one or more cellular responses exhibited by said mutant cells not contacted with said inhibitor;

(g) identifying one or more cellular responses exhibited by said mutant cells contacted with said inhibitor; and (h) comparing said one or more cellular responses in steps (d), (e), (f) and (g) to identify a pattern of cellular responses exhibited by said wild-type cells after said contact, wherein, when said wild-type signaling molecule pattern comprises one or more cellular responses characteristic of one or more cellular responses of the pattern of the inhibition of said mutant form of the wild-type signaling molecule, a pattern of one or more cellular responses attributable to selective inhibition of a wild-type signaling molecule is identified.

27. The method of claim 26 further comprising contacting said wild-type cells and said mutant cells with a stimulant in steps (d), (e), (f) and (g) to induce said one or more cellular responses.

28. The method of claim 26 wherein said stimulant is selected from the group consisting of hormones, cytokines, growth factors, heat, cold, light, metal ions, osmolarity changes, contact, homologous cells, heterologous cells, pressure, oxidative stress, natural products, plant extracts, marine organisms, synthetic compounds, combinatorial organic libraries, peptide libraries, organ tissue explants, and via cell transfer into animals.

* * * * *